(12) United States Patent
Hirsch et al.

(10) Patent No.: US 8,105,796 B2
(45) Date of Patent: Jan. 31, 2012

(54) REGULATION OF EXPRESSION OF PI3Kβ PROTEIN IN TUMORS

(75) Inventors: Emilio Hirsch, Turin (IT); Guido Forni, Turin (IT); Claudia Curcio, Turin (IT); Elisa Ciraolo, Turin (IT)

(73) Assignee: Universita' Degli Studi di Torino, Turin (IT)

( * ) Notice: Subject to any disclaimer, the term of this patent is extended or adjusted under 35 U.S.C. 154(b) by 3 days.

(21) Appl. No.: 12/526,681

(22) PCT Filed: Feb. 12, 2008

(86) PCT No.: PCT/IB2008/000382
§ 371 (c)(1), (2), (4) Date: Nov. 17, 2009

(87) PCT Pub. No.: WO2008/099280
PCT Pub. Date: Aug. 21, 2008

(65) Prior Publication Data
US 2010/0192240 A1    Jul. 29, 2010

Related U.S. Application Data

(60) Provisional application No. 60/901,323, filed on Feb. 15, 2007.

(51) Int. Cl.
*G01N 33/574* (2006.01)
(52) U.S. Cl. .......................... 435/7.23; 435/7.4
(58) Field of Classification Search ........................ None
See application file for complete search history.

(56) References Cited

U.S. PATENT DOCUMENTS
2006/0234246 A1  10/2006  Scott et al.
2007/0269432 A1  11/2007  Nakamura et al.

FOREIGN PATENT DOCUMENTS
WO        2005/028676        3/2005

OTHER PUBLICATIONS

Zhao et al, PNAS, 2005, 51:18443-18448.*
Benistant et al. "A specific function for phosphatidylinositol 3-kinase α (p85α-p110α) in cell survival and for phosphatidylinositol 3-kinase β (p85α-p110β) in de novo DNA synthesis of human colon carcinoma cells" *Oncogene*, vol. 19, No. 44, pp. 5083-5090 (Oct. 2000).
Bi et al. "Early embryonic lethality in mice deficient in the p110β catalytic subunit of PI 3-kinase" *Mammalian Genome*, vol. 13, No. 3, pp. 169-172 (Mar. 2002).
Brachmann et al. "Phosphoinositide 3-kinase catalytic subunit deletion and regulatory subunit deletion have opposite effects on insulin sensitivity in mice" *Molecular and Cellular Biology*, vol. 25, No. 5, pp. 1596-1607 (Mar. 2005).
Czauderna et al. "Functional studies of the PI(3)kinase signaling pathway employing synthetic and expressed siRNA" *Nucleic Acids Research*, vol. 31, No. 2, pp. 670-672 (Jan. 2003).
Czauderna et al. "Inducible shRNA expression for application in a prostate cancer mouse model" *Nucleic Acids Research*, vol. 31, No. 21, p. e127 (Nov. 2003).
Zhao, J.J. et al., "Genetic studies to facilitate targeting the PI3 kinase pathway in cancer", Proceedings of the American Association for Cancer Research Annual Meeting, vol. 47, p. 998, (Apr. 2006).
Stankewicz, C. et al., "A robust screen for inhibitors and enhancers of phosphoinositite-3 kinase (PI3K) activities by ratiometric fluorescence superquenching", Journal of Biomolecular Screening, vol. 11, No. 4, pp. 413-422, (Jun. 2006).
Int'l Search Report for PCT/IB2008/000382, mailed Aug. 21, 2008.
Written Opinion for PCT/IB2008/000382, mailed Aug. 21, 2008.

* cited by examiner

*Primary Examiner* — Misook Yu
*Assistant Examiner* — Mark Halvorson
(74) *Attorney, Agent, or Firm* — Nixon & Vanderhye P.C.

(57) ABSTRACT

We describe the use of PI3Kβ protein and/or its encoding gene for the screening for substances useful in the treatment of cancers, preferably breast cancers, as well as a method for the diagnosis of malignant cell growth comprising the measuring the expression of PI3Kβ. We also describe non-human transgenic animals as models for studying human pathologies, preferably breast cancer, being transgenic for having altered PI3Kβ and Neu-T expression.

9 Claims, 16 Drawing Sheets

Figure 11

```
ATGTGCTTCAGTTTCATAATGCCTCCTGCTATGGCAGACATCCTTGACATCTGGGCGGTGGATTCACAGATAGCATCTGATGG
CTCCATACCTGTGGATTTCCTTTTGCCCACTGGGATTTATATCCAGTTGGAGGTACCTCGGGAAGCTACCATTTCTTATATTA
AGCAGATGTTATGGAAGCAAGTTCACAATTACCCAATGTTCAACCTCCTTATGGATATTGACTCCTATATGTTTGCATGTGTG
AATCAGACTGCTGTATATGAGGAGCTTGAAGATGAAACACGAAGACTCTGTGATGTCAGACCTTTTCTTCCAGTTCTCAAATT
AGTGACAAGAAGTTGTGACCCAGGGGAAAAATTAGACTCAAAAATTGGAGTCCTTATAGGAAAAGGTCTGCATGAATTTGATT
CCTTGAAGGATCCTGAAGTAAATGAATTTCGAAGAAAAATGCGCAAATTCAGCGAGGAAAAAATCCTGTCACTTGTGGGATTG
TCTTGGATGGACTGGCTAAAACAAACATATCCACCAGAGCATGAACCATCCATCCCTGAAAACTTAGAAGATAAACTTTATGG
GGGAAAGCTCATCGTAGCTGTTCATTTTGAAAACTGCCAGGACGTGTTTAGCTTTCAAGTGTCTCCTAATATGAATCCTATCA
AAGTAAATGAATTGGCAATCCAAAAACGTTTGACTATTCATGGGAAGGAAGATGAAGTTAGCCCCTATGATTATGTGTTGCAA
GTCAGCGGGAGAGTAGAATATGTTTTTGGTGATCATCCACTAATTCAGTTCCAGTATATCCGGAACTGTGTGATGAACAGAGC
CCTGCCCCATTTTATACTTGTGGAATGCTGCAAGATCAAGAAAATGTATGAACAAGAAATGATTGCCATAGAGGCTGCCATAA
ATCGAAATTCATCTAATCTTCCTCTTCCATTACCACCAAAGAAAACACGAATTATTTCTCATGTTTGGGAAAATAACAACCCT
TTCCAAATTGTCTTGGTTAAGGGAAATAAACTTAACACAGAGGAAACTGTAAAAGTTCATGTCAGGGCTGGTCTTTTTCATGG
TACTGAGCTCCTGTGTAAAACCATCGTAAGCTCAGAGGTATCAGGGAAAAATGATCATATTTGGAATGAACCACTGGAATTTG
ATATTAATATTTGTGACTTACCAAGAATGGCTCGATTATGTTTTGCTGTTTATGCAGTTTTGGATAAAGTAAAAACGAAGAAA
TCAACGAAAACTATTAATCCCTCTAAATATCAGACCATCAGGAAAGCTGGAAAAGTGCATTATCCTGTAGCGTGGGTAAATAC
GATGGTTTTTGACTTTAAAGGACAATTGAGAACTGGAGACATAATATTACACAGCTGGTCTTCATTTCCTGATGAACTCGAAG
AAATGTTGAATCCAATGGGAACTGTTCAAACAAATCCATATACTGAAAATGCAACAGCTTTGCATGTTAAATTTCCAGAGAAT
AAAAAACAACCTTATTATTACCCTCCCTTCGATAAGATTATTGAAAAGGCAGCTGAGATTGCAAGCAGTGATAGTGCTAATGT
GTCAAGTCGAGGTGGAAAAAAGTTTCTTCCTGTATTCAAAGAAATCTTGGACAGGGATCCCTTGTCTCAACTGTGTGAAAATG
AAATGGATCTTATTTGGACTTTGCGACAAGACTGCCGAGAGATTTTCCCACAATCACTGCCAAAATTACTGCTGTCAATCAAG
TGGAATAAACTTGAGGATGTTGCTCAGCTTCAGGCGCTGCTTCAGATTTGGCCTAAACTGCCCCCCCGGGAGGCCCTAGAGCT
TCTGGATTTCAACTATCCAGACCAGTACGTTCGAGAATATGCTGTAGGCTGCCTGCGACAGATGAGTGATGAAGAACTTTCTC
AATATCTTTTACAACTGGTGCAAGTGTTAAAATATGAGCCTTTTCTTGATTGTGCCCTCTCTAGATTCCTATTAGAAAGAGCA
CTTGGTAATCGGAGGATAGGGCAGTTTCTATTTTGGCATCTTAGGTCAGAAGTGCACATTCCTGCTGTCTCAGTACAATTTGG
TGTCATCCTTGAAGCATACTGCCGGGGAAGTGTGGGGCACATGAAAGTGCTTTCTAAGCAGGTTGAAGCACTCAATAAGTTAA
AAACTTTAAATAGTTTAATCAAACTGAATGCCGTGAAGTTAAACAGAGCCAAAGGGAAGGAGGCCATGCATACCTGTTTAAAA
CAGAGTGCTTACCGGGAAGCCCTCTCTGACCTGCAGTCACCCCTGAACCCATGTGTTATCCTCTCAGAACTCTATGTTGAAAA
GTGCAAATACATGGATTCCAAAATGAAGCCTTGTGGCTGGTATACAATAACAAGGTATTTGGTGAGGATTCAGTTGGAGTGA
TTTTTAAAATGGTGATGATTTACGACAGGATATGTTGACACTCCAAATGTTGCGCTTGATGGATTTACTCTGGAAAGAAGCT
GGTTTGGATCTTCGGATGTTGCCTTATGGCTGTTTAGCAACAGGAGATCGCTCTGGCCTCATTGAAGTTGTGAGCACCTCTGA
AACAATTGCTGACATTCAGCTGAACAGTAGCAATGTCGCTGCTGCAGCAGCCTTCAACAAAGATGCCCTTCTGAACTGGCTTA
AAGAATACAACTCTGGGGATGACCTGGACCGAGCCATTGAGGAATTTACACTGTCCTGTGCTGGCTACTGTGTAGCTTCTTAT
GTCCTTGGGATTGGTGACAGACATAGTGACAACATCATGGTCAAAAAAACTGGCCAGCTCTTCCACATTGACTTTGGACATAT
TCTTGGAAATTTCAAATCTAAGTTTGGCATTAAAAGGGAGCGAGTGCCTTTTATTCTTACCTATGATTTCATCCATGTCATTC
AACAAGGAAAAACAGGAAATACAGAAAAGTTTGGCCGGTTCCGCCAGTGTTGTGAGGATGCATATCTGATTTTACGACGGCAT
GGGAATCTCTTCATCACTCTCTTTGCGCTGATGTTGACTGCAGGGCTTCCTGAACTCACATCAGTCAAAGATATACAGTATCT
TAAGGACTCTCTTGCATTAGGGAAGAGTGAAGAAGAAGCACTCAAACAGTTTAAGCAAAAATTTGATGAGGCGCTCAGGGAAA
GCTGGACTACTAAAGTGAACTGGATGGCCCACACAGTTCGGAAAGACTACAGATCTTAA
```

Figure 12

```
ATGTGCTTCAGTTTCATAATGCCTCCTGCTATGGCAGACATCCTTGACATCTGGGCGGTGGATTCACAGATAGCATCTGATGG
CTCCATACCTGTGGATTTCCTTTTGCCCACTGGGATTTATATCCAGTTGGAGGTACCTCGGGAAGCTACCATTTCTTATATTA
AGCAGATGTTATGGAAGCAAGTTCACAATTACCCAATGTTCAACCTCCTTATGGATATTGACTCCTATATGTTTGCATGTGTG
AATCAGACTGCTGTATATGAGGAGCTTGAAGATGAAACACGAAGACTCTGTGATGTCAGACCTTTTCTTCCAGTTCTCAAATT
AGTGACAAGAAGTTGTGACCCAGGGGAAAAATTAGACTCAAAAATTGGAGTCCTTATAGGAAAAGGTCTGCATGAATTTGATT
CCTTGAAGGATCCTGAAGTAAATGAATTTCGAAGAAAATGCGCAAATTCAGCGAGGAAAAAATCCTGTCACTTGTGGGATTG
TCTTGGATGGACTGGCTAAAACAAACATATCCACCAGAGCATGAACCATCCATCCCTGAAAACTTAGAAGATAAACTTTATGG
GGGAAAGCTCATCGTAGCTGTTCATTTTGAAAACTGCCAGGACGTGTTTAGCTTTCAAGTGTCTCCTAATATGAATCCTATCA
AAGTAAATGAATTGGCAATCCAAAAACGTTTGACTATTCATGGGAAGGAAGATGAAGTTAGCCCCTATGATTATGTGTTGCAA
GTCAGCGGGAGAGTAGAATATGTTTTTGGTGATCATCCACTAATTCAGTTCCAGTATATCCGGAACTGTGTGATGAACAGAGC
CCTGCCCCATTTTATACTTGTGGAATGCTGCAAGATCAAGAAAATGTATGAACAAGAAATGATTGCCATAGAGGCTGCCATAA
ATCGAAATTCATCTAATCTTCCTCTTCCATTACCACCAAAGAAAACACGAATTATTTCTCATGTTTGGGAAAATAACAACCCT
TTCCAAATTGTCTTGGTTAAGGGAAATAAACTTAACACAGAGGAAACTGTAAAAGTTCATGTCAGGGCTGGTCTTTTTCATGG
TACTGAGCTCCTGTGTAAAACCATCGTAAGCTCAGAGGTATCAGGGAAAAATGATCATATTTGGAATGAACCACTGGAATTTG
ATATTAATATTTGTGACTTACCAAGAATGGCTCGATTATGTTTTGCTGTTTATGCAGTTTTGGATAAAGTAAAAACGAAGAAA
TCAACGAAAACTATTAATCCCTCTAAATATCAGACCATCAGGAAAGCTGGAAAAGTGCATTATCCTGTAGCGTGGGTAAATAC
GATGGTTTTTGACTTTAAAGGACAATTGAGAACTGGAGACATAATATTACACAGCTGGTCTTCATTTCCTGATGAACTCGAAG
AAATGTTGAATCCAATGGGAACTGTTCAAACAAATCCATATACTGAAAATGCAACAGCTTTGCATGTTAAATTTCCAGAGAAT
AAAAAACAACCTTATTATTACCCTCCCTTCGATAAGATTATTGAAAAGGCAGCTGAGATTGCAAGCAGTGATAGTGCTAATGT
GTCAAGTCGAGGTGGAAAAAAGTTTCTTCCTGTATTGAAAGAAATCTTGGACAGGGATCCCTTGTCTCAACTGTGTGAAAATG
AAATGGATCTTATTTGGACTTTGCGACAAGACTGCCAGAGATTTTCCCACAATCACTGCCAAAATTACTGCTGTCAATCAAG
TGGAATAAACTTGAGGATGTTGCTCAGCTTCAGGCGCTGCTTCAGATTTGGCCTAAACTGCCCCCCCGGGAGGCCCTAGAGCT
TCTGGATTTCAACTATCCAGACCAGTACGTTCGAGAATATGCTGTAGGCTGCCTGCGACAGATGAGTGATGAAGAACTTTCTC
AATATCTTTTACAACTGGTGCAAGTGTTAAAATATGAGCCTTTTCTTGATTGTGCCCTCTCTAGATTCCTATTAGAAAGAGCA
CTTGGTAATCGGAGGATAGGGCAGTTTCTATTTTGGCATCTTAGGTCAGAAGTGCACATTCCTGCTGTCTCAGTACAATTTGG
TGTCATCCTTGAAGCATACTGCCGGGGAAGTGTGGGGCACATGAAAGTGCTTTCTAAGCAGGTTGAAGCACTCAATAAGTTAA
AAACTTTAAATAGTTTAATCAAACTGAATGCCGTGAAGTTAAACAGAGCCAAAGGGAAGGAGGCCATGCATACCTGTTTAAAA
CAGAGTGCTTACCGGGAAGCCCTCTCTGACCTGCAGTCACCCCTGAACCCATGTGTTATCCTCTCAGAACTCTATGTTGAAAA
GTGCAAATACATGGATTCCAAAATGAAGCCTTTGTGGCTGGTATACAATAACAAGGTATTTGGTGAGGATTCAGTTGGAGTGA
TTTTTAGAAATGGTGATGATTTACGACAGGATATGTTGACACTCCAAATGTTGCGCTTGATGGATTTACTCTGGAAAGAAGCT
GGTTTGGATCTTCGGATGTTGCCTTATGGCTGTTTAGCAACAGGAGATCGCTCTGGCCTCATTGAAGTTGTGAGCACCTCTGA
AACAATTGCTGACATTCAGCTGAACAGTAGCAATGTGGCTGCTGCAGCAGCCTTCAACAAAGATGCCCTTCTGAACTGGCTTA
AGAATACAACTCTGGGGATGACCTGGACCGAGCCATTGAGGAATTTACACTGTCCTGTGCTGGCTACTGTGTAGCTTCTTAT
GTCCTTGGGATTGTGACAGACATAGTGACAACATCATGGTCAAAAAAACTGGCCAGCTCTTCCACATTGACTTTGGACATAT
TCTTGGAAATTTCAAATCTAAGTTTGGCATTAAAAGGGAGCGAGTGCCTTTTATTCTTACCTATGATTCATCCATGTCATTC
AACAAGGAAAAACAGGAAATACAGAAAAGTTTGGCCGGTTCCGCCAGTGTTGTGAGGATGCATATCTGATTTTACGACGGCAT
GGGAATCTCTTCATCACTCTCTTTGCGCTGATGTTGACTGCAGGGCTTCCTGAACTCACATCAGTCAAAGATATACAGTATCT
TAAGGACTCTCTTGCATTAGGGAAGAGTGAAGAAGAAGCACTCAAACAGTTTAAGCAAAAATTTGATGAGGCGCTCAGGGAAA
GCTGGACTACTAAAGTGAACTGGATGGCCCACACAGTTCGGAAAGACTACAGATCTTAA
```

Figure 13

```
MCFSFIMPPAMADILDIWAVDSQIASDGSIPVDFLLPTGIYIQLEVPREATISYIKQMLWKQVHNYPMFNLLMDIDSYMFACV
NQTAVYEELEDETRRLCDVRPFLPVLKLVTRSCDPGEKLDSKIGVLIGKGLHEFDSLKDPEVNEFRRKMRKFSEEKILSLVGL
SWMDWLKQTYPPEHEPSIPENLEDKLYGGKLIVAVHFENCQDVFSFQVSPNMNPIKVNELAIQKRLTIHGKEDEVSPYDYVLQ
VSGRVEYVFGDHPLIQFQYIRNCVMNRALPHFILVECCKIKKMYEQEMIAIEAAINRNSSNLPLPLPPKKTRIISHVWENNNP
FQIVLVKGNKLNTEETVKVHVRAGLFHGTELLCKTIVSSEVSGKNDHIWNEPLEFDINICDLPRMARLCFAVYAVLDKVKTKK
STKTINPSKYQTIRKAGKVHYPVAWVNTMVFDFKGQLRTGDIILHSWSSFPDELEEMLNPMGTVQTNPYTENATALHVKFPEN
KKQPYYYPPFDKIIEKAAEIASSDSANVSSRGGKKFLPVLKEILDRDPLSQLCENEMDLIWTLRQDCREIFPQSLPKLLLSIK
WNKLEDVAQLQALLQIWPKLPPREALELLDFNYPDQYVREYAVGCLRQMSDEELSQYLLQLVQVLKYEPFLDCALSRFLLERA
LGNRRIGQFLFWHLRSEVHIPAVSVQFGVILEAYCRGSVGHMKVLSKQVEALNKLKTLNSLIKLNAVKLNRAKGKEAMHTCLK
QSAYREALSDLQSPLNPCVILSELYVEKCKYMDSKMKPLWLVYNNKVFGEDSVGVIFKNGDDLRQDMLTLQMLRLMDLLWKEA
GLDLRMLPYGCLATGDRSGLIEVVSTSETIADIQLNSSNVAAAAAFNKDALLNWLKEYNSGDDLDRAIEEFTLSCAGYCVASY
VLGIGDRHSDNIMVKKTGQLFHIDFGHILGNFKSKFGIKRERVPFILYDFIHVIQQGKTGNTEKFGRFRQCCEDAYLILRRH
GNLFITLFALMLTAGLFELTSVKDIQYLKDSLALGKSEEEALKQFKQKFDEALRESWTTKVNWMAHTVRKDYRS
```

Figure 14

```
MCFSFIMPPAMADILDIWAVDSQIASDGSIPVDFLLPTGIYIQLEVPREATISYIKQMLWKQVHNYPMFNLLMDIDSYMFACV
NQTAVYEELEDETRRLCDVRPFLPVLKLVTRSCDPGEKLDSKIGVLIGKGLHEFDSLKDPEVNEFRRKMRKFSEEKILSLVGL
SWMDWLKQTYPPEHEPSIPENLEDKLYGGKLIVAVHFENCQDVFSFQVSPNMNPIKVNELAIQKRLTIHGKEDEVSPYDYVLQ
VSGRVEYVFGDHPLIQFQYIRNCVMNRALPHFILVECCKIKKMYEQEMIAIEAAINRNSSNLPLPLPPKKTRIISHVWENNNP
FQIVLVKGNKLNTEETVKVHVRAGLFHGTELLCKTIVSSEVSGKNDHIWNEPLEFDINICDLPRMARLCFAVYAVLDKVKTKK
STKTINPSKYQTIRKAGKVHYPVAWVNTMVFDFKGQLRTGDIILHSWSSFPDELEEMLNPMGTVQTNPYTENATALHVKFPEN
KKQPYYYPPFDKIIEKAAEIASSDSANVSSRGGKKFLPVLKEILDRDPLSQLCENEMDLIWTLRQDCREIFPQSLPKLLLSIK
WNKLEDVAQLQALLQIWPKLPPREALELLDFNYPDQYVREYAVGCLRQMSDEELSQYLLQLVQVLKYEPFLDCALSRFLLERA
LGNRRIGQFLFWHLRSEVHIPAVSVQFGVILEAYCRGSVGHMKVLSKQVEALNKLKTLNSLIKLNAVKLNRAKGKEAMHTCLK
QSAYREALSDLQSPLNPCVILSELYVEKCKYMDSKMKPLWLVYNNKVFGEDSVGVIFRNGDDLRQDMLTLQMLRLMDLLWKEA
GLDLRMLPYGCLATGDRSGLIEVVSTSETIADIQLNSSNVAAAAAFNKDALLNWLKEYNSGDDLDRAIEEFTLSCAGYCVASY
VLGIGDRHSDNIMVKKTGQLFHIDFGHILGNFKSKFGIKRERVPFILYDFIHVIQQGKTGNTEKFGRFRQCCEDAYLILRRH
GNLFITLFALMLTAGLFELTSVKDIQYLKDSLALGKSEEEALKQFKQKFDEALRESWTTKVNWMAHTVRKDYRS
```

Figure 15

```
CTGGTCCGGGCCCCCCCTCGAGGTCGACGGTATCGATAAGCTTGATATCGAATTCCTGCAGGTAAGAAAGTAAGT
NGTCAGGTAATACATGCTTCTAATTAATGGTGAGGCTGTAAGAGGTGGGAAGGTTTCTGCAAGTTCCTGTGTTCA
GTGTAAGACTCCTGCCTGGCCCAGCCTCCAAAAGAAAAAAATGTTGTCCAGTAGTTTTCATGAGCAAAAATGAAA
ACCTACAGACTATCTATTAAGTCTTGTAACTTGTAAAACACATGTTCTTCTCATGCCATACGACTGGGACTGAAA
CACTGACTCTCTGGGGTCTTCAGCCAGACTTCAGACACGATCCGTGTTCATGAGTCGTGAACATTGCAAGTTCTC
AGCCTTTCTGACTCAGACAAAGAACTAACCACTGGCTCCCTTGTGTCTCCAGCTTGTCAACTTTGCAGATCCTGA
CGTGCCATTGTATACTTCCAAAACCATTCAAGACAGATCTTGCTAGTAAGTCGCCAAATACATCTGTGTGTTCTG
ATGTATCTATGATACATGTCAATAGTCACATGTAAGCATGCACAGTGATCCTCTCTTAGCCGTTCGTTGTTACAG
GAAACCCTCGGGCATTCACGCACCTGTCTCTTCTGTTTGTAATGCACATCTCAGCCAAGGGAGTCAGAAAAGAAA
AGGCTGGAGAGATGCGCGAANGTGTTGTTTTTTTGTTTTTTACTTTTTATTAACACAGAACTAGAGCACCCAAC
CTTTCTAGCAATCTGCATCTGCAGCCCGGGGGATCCACCAGTCTAGACGCCGCCACCGCGGGAGAC
```

Figure 16

```
AGCAGCCTTCAACAAAGATGCCCTTCTGAACTGGCTTAAAGAATACAACTCTGGGGATGA
CCTGGACCGAGCCATTGAGGAATTTACACTGTCCTGTGCTGGCTACTGTGTAGCTTCTTA
TGTCCTTGGGATTGGTGACAGACATAGTGACAACATCATGGTCAAAAAAACTGGCCAGCT
CTTCCACATTGACTTTGGACATATTCTTGGAAATTTCAAATCTAAGTTTGGCATTAAAAG
GGAGCGAGTGCCTTTTATTCTTACCTATGATTTCATCCATGTCATTCAACAAGGAAAAAC
AGGAAATACAGAAAAGTTTGGCCGGTTCCGCCAGTGTTGTGAGGATGCATATCTGATTTT
ACGACGGCATGGGAATCTCTTCATCACTCTCTTTGCGCTGATGTTGACTGCA
```

Figure 18

```
PIK3CB    gi|5453894|ref|NP_006210.1    804-FKNGDDLRQDM-814 (Homo sapiens)
Pik3cb    gi|16758236|ref|NP_445933.1   804-FKNGDDLRQDM-814 (Rattus norvegicus)
Pik3cb    gi|29789235|ref|NP_083370.1   798-FKNGDDLRQDM-808 (Mus musculus)
```

Figure 17
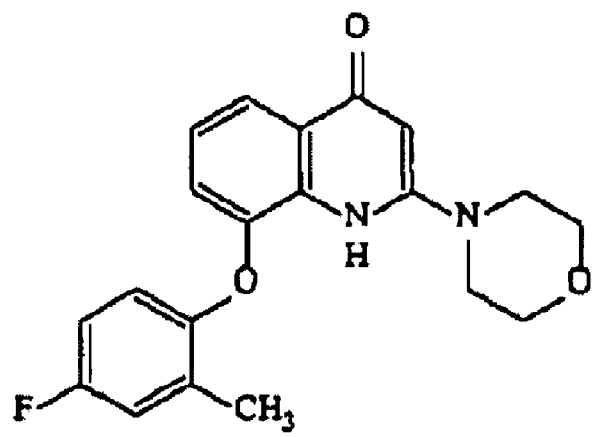
TGX-155
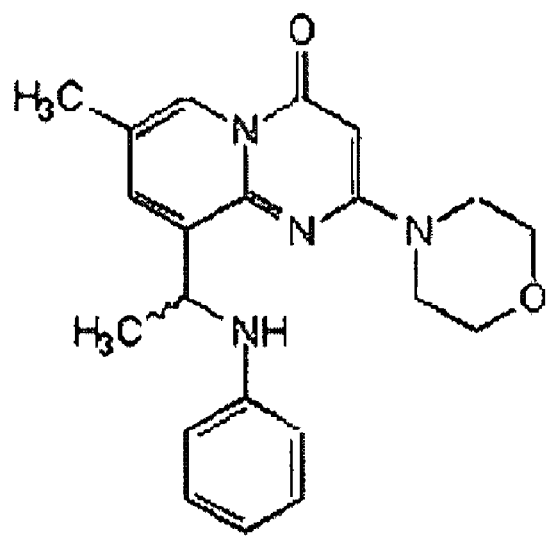
TGX-221

REGULATION OF EXPRESSION OF PI3Kβ PROTEIN IN TUMORS

This application is the U.S. national phase under 35 U.S.C. 371 of International Application No. PCT/IB2008/000382, filed 12 Feb. 2008, which designated the U.S. and claims the benefit of U.S. Provisional Application No. 60/901,323 filed 15 Feb. 2007; the entire contents of which are hereby incorporated by reference.

TECHNICAL FIELD OF THE INVENTION

The present invention relates to the area of PI3Kβ protein. More particularly, the present invention relates to the expression of PI3Kβ in cancers and its regulation.

BACKGROUND OF THE INVENTION

Phosphoinositide 3-kinases (PI3Ks) are signaling molecules involved in numerous cellular functions such as cell cycle, cell motility and apoptosis. PI3Ks are protein and lipid kinases that produce second messenger molecules activating several target proteins including small GTPases like Ras, Rho, Rac and Cdc42 and serine/threonine kinases like PDK1 and Akt/PKB. This latter kinase phosphorylates and inhibits two important players in the apoptotic machinery, BAD and Caspase-9. Furthermore, PKB modulates the activity of GSK3, mTOR, p70S6K and FOX transcription factors, eventually controlling cell proliferation. Accordingly to this view, PI3Ks are known to act as oncogenes by amplification or mutation (Cully et al., 2006; Vivanco and Sawyers, 2002). Moreover, PTEN, the enzyme which de-phosphorylates phosphoinositides at the D-3 hydroxy position of the inositol ring, functions as a potent anti-oncogene. Altogether these observations strongly indicate that metabolism of PtdIns 3-phosphates is directly involved in the oncogenic process and that PI3Ks might be key regulators of the transformed phenotype.

PI3Ks are divided in three classes and class I comprises four different PI3Ks named α, β, γ and δ. Class IA PI3Ks are mainly activated by tyrosine kinase receptors and are heterodimers composed of a p110 catalytic subunit and a p85 regulatory subunit. PI3Kβ (p110β) is a class IA member that is ubiquitously expressed and possesses the unique feature of being activated not only by tyrosine kinase receptors, but also by G protein-coupled receptors (Vanhaesebroeck et al., 2001). Presently, little is known about the specific in vivo function of the PI3Kβ isoform.

SUMMARY OF THE INVENTION

It is an object of the present invention to provide reagents and methods for regulating expression, function and/or activity of human PI3Kβ enzyme. In a preferred embodiment the present invention concerns methods for the development of therapeutical approaches for the treatment of cancer.

It is, thus, an object of the present invention the use of PI3Kβ protein or fragments thereof and/or the polynucleotide encoding for PI3Kβ protein or fragments thereof as target for the development of therapeutical approaches for treatment of cancer and, more specifically, for the screening for substances useful in the treatment of patients suffering from a cancer. In a preferred embodiment of the invention the cancer is a breast cancer. More specifically, it is an object of the present invention the use of i) a polynucleotide encoding and/or ii) a polypeptide comprising at least a portion of the p110β catalytic subunit of PI3Kβ protein for screening for pharmacologically active agents useful in the treatment of cancer.

It is a still further object of the present invention to provide for methods for the diagnosis or prognosis of malignant cell growth comprising the measurement of the expression of PI3Kβ gene and HER2/Neu (also known as ErbB-2) gene and/or activity of PI3Kβ protein and HER2/Neu protein in a biological sample from a patient.

The invention concerns also non-human transgenic animals (Boggio et al., 1998) as model study for human pathologies, being transgenic for having altered at least PI3Kβ expression, and, more preferably, reduced enzymatic activity of PI3Kβ protein, wherein the transgenic animal is suitable to develop insulin resistance and Erbb2-driven mammary gland cancer protection. Preferably the human pathology is a cancer, more preferably the cancer is a breast cancer.

It is a further object of the invention cells derivable from the non-human transgenic animal of the invention. The invention concerns different uses of the cells for the selection of molecules pharmacologically effective in triggering the expression and/or function/activity of PI3Kβ enzyme.

According to the present invention, said objects are achieved thanks to the solution having the characteristics referred to specifically in the ensuing claims. The claims form integral part of the technical teaching herein provided in relation to the present invention.

BRIEF DESCRIPTION OF THE DRAWINGS

FIG. 11. Nucleic acid sequence for wild-type *Homo sapiens* phosphoinositide-3-kinase, catalytic, beta polypeptide (PIK3CB), mRNA [3213 bp], corresponding to SEQ ID NO.: 1.

FIG. 12. Nucleic acid sequence for A2414G Mutant (resulting in K805R mutation) *Homo sapiens* phosphoinositide-3-kinase, catalytic, beta polypeptide, kinase death (PIK3CB), mRNA [3213 bp], corresponding to SEQ ID NO.:2.

FIG. 13. Aminoacid sequence for wild-type Phosphoinositide-3-kinase, catalytic, beta polypeptide [*Homo sapiens*] [1070 aa], corresponding to SEQ ID NO.:3.

FIG. 14. Aminoacid sequence for K805R Mutant Phosphoinositide-3-kinase, catalytic, beta polypeptide kinase death [*Homo sapiens*] [1070 aa], corresponding to SEQ ID NO.:4.

FIG. 15. Probe 1 was used to detect homologous recombination, corresponding to SEQ ID NO.:5.

FIG. 16. Probe 2 was used to detect Cre-mediated excision of the wild-type cDNA, corresponding to SEQ ID NO.:6.

FIG. 17. Chemical structure of TGX-221 and TGX-155 compounds.

FIG. 18. Partial sequence of the ATP-binding site of PI3Kbeta enzyme of different origins (human, rat and mouse; SEQ ID NO.:7 repeated three times).

DETAILED DESCRIPTION OF THE INVENTION

Figure 1:
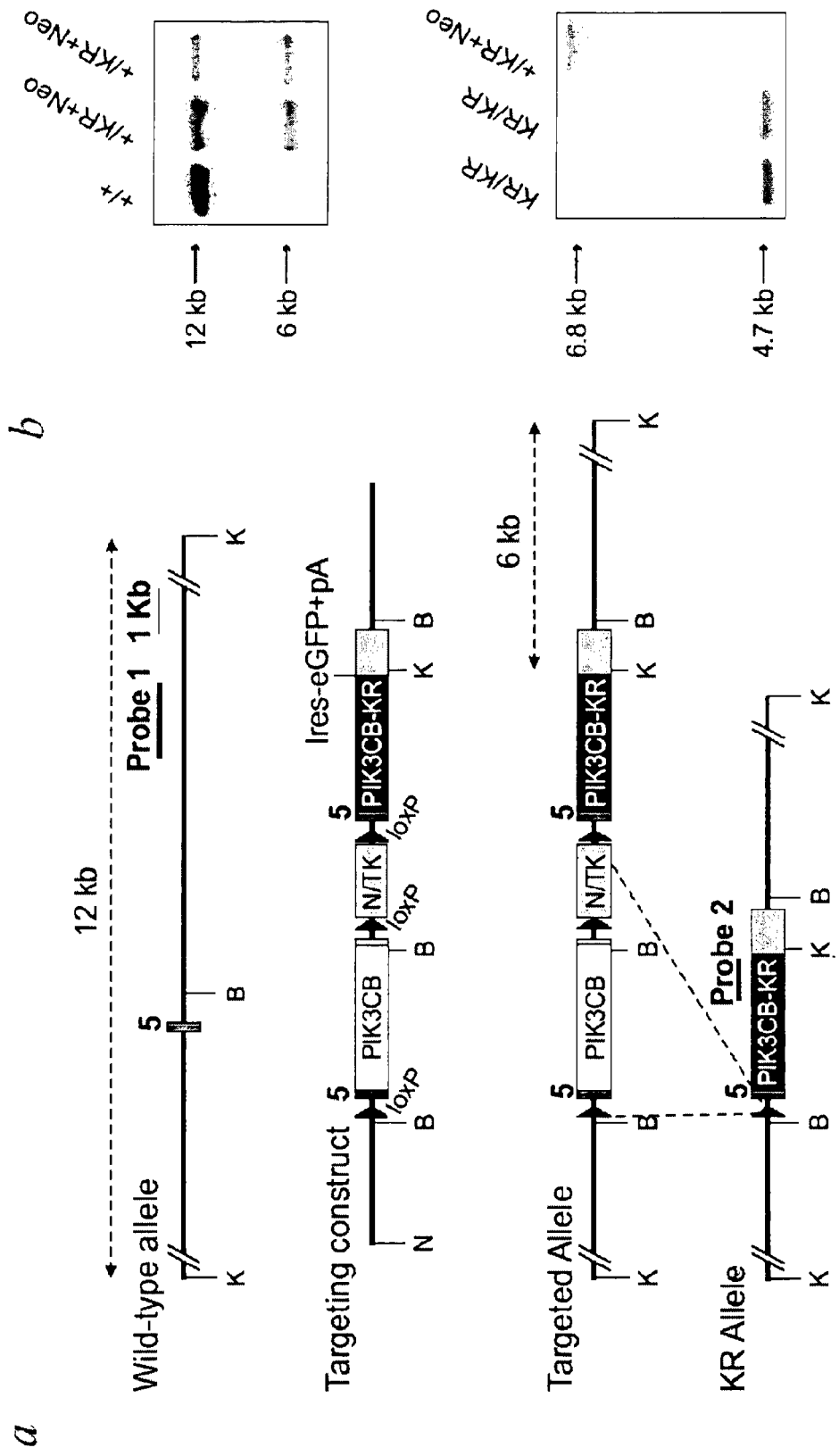
FIG. 1. a) Description of the gene targeting strategy and structure of the PI3Kβ gene (PIC3CB, SEQ ID NO.:1 and 3—FIGS. 11 and 13) and the PI3Kβ$^{KR}$ allele (SEQ ID NO.:2 and 4—FIGS. 12 and 14) carrying the K805R mutation known to abrogate the kinase activity. Restriction sites: K, KpnI; B, BamHI; N, NotI. Triangles: LoxP sites. N/TK box: neomycin/thymidine kinase double selection cassette. 5: fifth coding exon. Drawing of the cassettes is not in scale. Probe 1 (SEQ ID NO.:5—FIG. 15) was used to detect homologous recombination. Probe 2 SEQ ID NO.:6—FIG. 16) was used to detect Cre-mediated excision of the wild-type cDNA. b) Southern blot analysis with probe 1 (upper panel) and probe 2 (lower panel) of ES and tail-derived genomic DNA digested with KpnI and BamHI, respectively.

The present invention will now be described in detail in relation to some preferred embodiments by way of non-limiting examples.

The present invention relates to a catalytically inactive form of phospho inositol 3 kinase of type β—PI3Kβ—carrying a K805R mutation (PI3KβKR) (SEQ ID NO.:2 and 4). More specifically, homozygous mice expressing the mutant PI3Kβ$^{KR}$ were generated, which were viable and reached adulthood. Such homozygous mice were born accordingly to a distorted Mendelian ratio, were phenotypically characterized by a small but significant growth retardation, a significantly impaired phosphorylation of Akt/PKB in response to growth factors (INS, IGF1), insulin resistance as well as reduced testis size and block of spermatogenesis.

Most of all, said mice were intercrossed with mice expressing the HER-2/neu oncogene in the mammary gland (Boggio et al., 1998). The mutant mice homozygous for the PI3Kβ$^{KR}$ allele and heterozygous for the HER-2/neu oncogene, showed a significant delay in the development of the first and subsequent breast tumors, which also had smaller dimensions compared to wild-type controls (mice expressing the HER-2/neu oncogene). Thus the mutation or chronic reduction of PI3Kβ function protects from HER-2/neu-driven tumor formation.

Testing of PI3Kβ expression levels can also be used for diagnostic purposes to determine the prognosis of cancer or propensity to develop or worsen an already developed type II diabetes.

The invention provides, thus, human PI3Kβ protein as a target protein for the identification of compounds which may act as antagonists/inhibitors of PI3Kβ protein, and can be useful in the treatment of patients suffering from a cancer, in particular breast cancer.

The present invention provides also human PI3Kβ polynucleotide as a target polynucleotide which can be used to identify compounds which may interfere with PI3Kβ protein expression, in particular down-regulation, and can be useful in the treatment of patients suffering from a cancer.

Screening Methods

The invention provides assays for screening test compounds which bind to or modulate the expression/function of PI3Kβ protein.

A test compound preferably binds to PI3Kβ. More preferably, a test compound decreases a biological activity mediated via PI3Kβ by at least about 10, preferably about 50, more preferably about 75, 90, or 100% relative to the absence of the test compound.

A further test compound preferably regulates expression of PI3Kβ. More preferably, a test compound down-regulates the expression of PI3Kβ encoding gene by at least about 10, preferably about 50, more preferably about 75, 90, or 100% relative to the absence of the test compound.

Test Compounds

Test compounds can be pharmacological agents, small interfering RNA, peptides or proteins already known in the art or can be compounds previously unknown to have any pharmacological activity. Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Binding Assays

For binding assays, the test compound is preferably a small molecule which binds to and occupies the ligand binding site of PI3Kβ, thereby making the ligand binding site inaccessible to substrate such that normal biological activity is prevented. Examples of such small molecules include, but are not limited to, organic molecules, small peptides or peptide-like molecules. Potential ligands which bind to a polypeptide of the invention include, but are not limited to, the natural ligands of PI3Kβ and analogues or derivatives thereof. Natural ligands of PI3Kβ include but are not limited to: adenosin triphosphate (ATP), phosphatidyl inositol, phosphatidyl inositol phosphate, phosphatidyl inositol (4,5) bisphosphate.

In binding assays, either the test compound or PI3Kβ can comprise a detectable label, such as a fluorescent, radioisotopic, chemiluminescent, or enzymatic label, such as horseradish peroxidase, alkaline phosphatase, or luciferase. Detection of a test compound which is bound to the PI3Kβ can then be accomplished, for example, by direct counting of radioemission, by scintillation counting, or by determining conversion of an appropriate substrate to a detectable product.

Functional Assays

Test compounds can be tested systemically or locally (for example intra-nipple) for the ability to decrease a biological effect or activity and/or expression of PI3Kβ enzyme.

Such biological effects can be determined using the functional assays described in the specific examples, below. Functional assays can be carried out after contacting either a purified portion or a full-length PI3Kβ polypeptide, a cell membrane preparation, PI3Kβ polypeptide with a test compound. For example, screening assays for identifying compounds that modify functionality of PI3Kβ may be practiced using peptides or polypeptides corresponding to particular regions or domains of a full-length PI3Kβ. A test compound which decreases a functional activity of a PI3Kβ by at least about 10, preferably about 50, more preferably about 75, 90, or 100% is identified as a potential agent for decreasing PI3Kβ activity.

PI3Kβ Gene Expression

In another embodiment, test compounds which decrease PI3Kβ gene expression are identified. A PI3Kβ polynucleotide is contacted with a test compound, and the expression of an RNA or polypeptide product of the PI3Kβ polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of PI3Kβ mRNA or polypeptide expression in the cells can be determined by methods well known in the art for detecting mRNA or polypeptide. Either qualitative or quantitative methods can be used. The presence of polypeptide products of a PI3Kβ polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labelled amino acids into a PI3Kβ polypeptide.

Such screening can be carried out either in a cell-free assay system or in an intact cell. Any cell which expresses a PI3Kβ polynucleotide can be used in a cell-based assay system. The PI3Kβ polynucleotide can be naturally occurring in the cell or can be introduced using techniques such as those described above. Either a primary culture or an established cell line, such as CHO or human embryonic kidney 293 cells, can be used.

Therapeutic Indications and Methods

PI3Kβ is responsible for many biological functions, and in particular is agonist to the proliferation of tumor cells. Accordingly, it is desirable to find compounds and drugs which inhibit the function of PI3Kβ. For example, compounds which inhibit PI3Kβ expression and/or activity/functionality may be employed for therapeutic purposes, such as the treatment of tumors.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, a small molecule pharmacological inhibitor, a siRNA, an antisense nucleic acid molecule, a specific antibody, etc.) can be used in an animal model to determine the efficacy, toxicity, or side effects of treatment with such an agent.

Furthermore, this invention pertains to uses of novel agents identified by the above described screening assays for treatments as described herein.

Compounds identified using the screening methods above can be used for the treatment of tumors, and for example of Her-2 positive breast cancer.

EXAMPLES

Example 1

Generation and Characterization of a Mouse Model Expressing a Catalytically Inactive Form of PI3Kβ

To study the role of PI3Kβ in vivo, the present inventors generated a mouse mutant expressing a catalytically inactive form of human PI3Kβ (SEQ ID NO.:3) by mutating an aminoacid in the ATP-binding site of PI3Kβ, wherein the ATP-biding site of PI3Kβ is comprised between aminoacid 801 and aminoacid 1065 of SEQ ID NO.:3. SEQ ID NO.:7 (consisting of the aminoacid sequence FKNGDDLRQDM) represents the consensus sequence of eleven aminoacids of the ATP-biding site highly conserved among PI3Kβ proteins of different origins (mouse, human, rat, see FIG. 18) located, with respect to SEQ ID NO.:3, between aminoacid 804 and aminoacid 814. More specifically, the mutation involved the first lysine in the ATP-biding site (at position 805 of SEQ ID NO.:3 or at position 2 of the consensus sequence represented by SEQ ID NO.:7), wherein lysine was mutated with arginine (K->R) (PI3Kβ$^{KR}$), thus leading to the catalytically inactive form of human PI3Kβ showed in SEQ ID NO.:4.

For the generation of such mutant mouse, the present inventors isolated ES cells carrying a mutant allele that, taking advantage of the Cre/loxP technology, was engineered to conditionally substitute PI3Kβ (p110β) with its catalytically inactive form. In these ES cells, a loxP site was positioned upstream exon 5 of PI3Kβ. The exon 5 itself was then fused in frame with the wild-type human PI3Kβ cDNA, followed by a polyadenylation signal and a floxed neomycin resistance cassette. Downstream this minigene, a duplicated intron5/exon6 was inserted. The duplicated exons was this time fused to a PI3Kβ cDNA carrying the lysine-arginine (KR) substitution (Wymann et al., 1996), known to abrogate the kinase activity (see FIG. 1). These heterozygous cells (bearing what we termed the PI3Kβ$^{WT/Neo}$ genotype) have been transiently transfected with a Cre expressing construct and clones have been isolated that carry the PI3Kβ$^{WT/Cond}$ and the genotypes (see FIG. 1). Mice were then generated to carry PI3Kβ$^{KR}$ allele, causing the expression of the kinase dead mutant.

Figure 2:
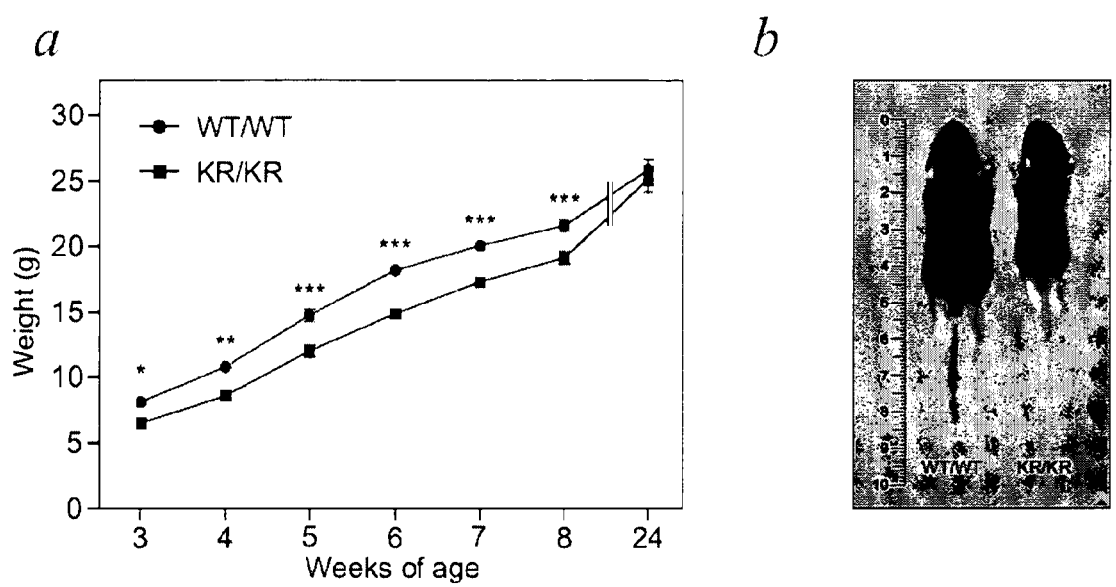
FIG. 2. Growth retardation in mice homozygous for the PI3Kβ$^{KR}$ allele. a) Weight gain over 8 weeks of age in wild-type and PI3Kβ$^{KR/KR}$ pups. Weight differences disappear at 24 weeks. b) Nose-to-tail length comparison of 1 week old wild-type (left) and PI3Kβ$^{KR/KR}$ littermates.

In contrast to a previous report showing that lack of PI3Kβ leads to an embryonic lethal phenotype (Bi et al., 2002), inter-breeding PI3Kβ$^{KR/WT}$ heterozygous mice produced surviving homozygous PI3Kβ$^{KR/KR}$ offsprings, which could reach adulthood. However, the number of PI3Kβ$^{KR/KR}$ mice, derived from crosses of PI3Kβ$^{KR/WT}$ heterozygous animals, showed a distorted Mendelian ratio: among 372 offsprings, the number of homozygous mutants was 50% less than expected (P<0.0001 by $\chi^2$) (see table 1). This finding may be explained by a partially penetrant embryonic lethality, in accordance with what reported for the total ablation of PI3Kβexpression (Bi et al., 2002). PI3Kβ$^{KR/KR}$ viable mice showed a small but significant growth retardation, in fact mutant mice were about 20% lighter than wild-type controls (P<0.001 by two way ANOVA; n=43) (see FIG. 2a) and showed significantly shorter nose-tail distance (see FIG. 2b). This appeared already at birth and was retained up to 8 weeks of age when mutant mice slowly started to catch up with controls. This finding is in agreement with several other reports indicating growth reduction in mutants of PI3K signaling pathway elements, for example PDK1 (Lawlor et al., 2002).

TABLE 1

| Genotyped analyzed | PI3Kβ$^{+/+}$ | PI3Kβ$^{KR/+}$ | PI3JKβ$^{KR/KR}$ | |
|---|---|---|---|---|
| 372 | 102 | 220 | 50 | P < 0.0001 |

Example 2

Kinase Independent Activity of p110β

Figure 3:
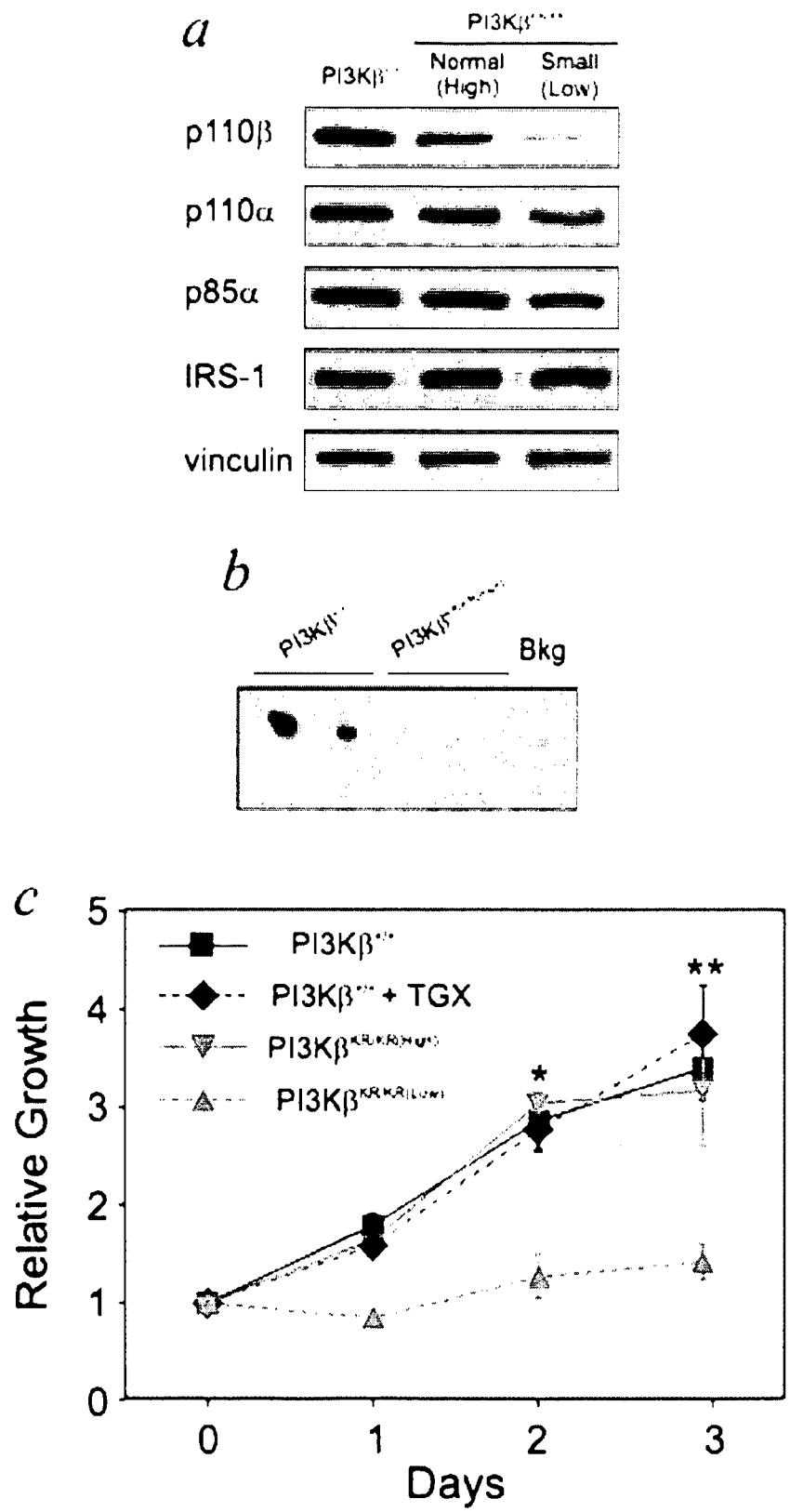
FIG. 3. PI3Kβ$^{KR}$ expression dosage inversely correlates with phenotype severity. a) MEFs were derived from normal (PI3Kβ$^{KR/KR(High)}$) or abnormal PI3Kβ$^{KR/KR\ (Low)}$) embryos and the expression level of the PI3Kβ$^{KR/KR}$ protein was analyzed by SDS-PAGE and immunoblotting, using the indicated antibodies. b) analysis of p110β catalytic activity. Lipid kinase assay was performed on p110β immunoprecipitated from wild type (PI3Kβ$^{+/+}$) and PI3Kβ$^{KR/KR(High)}$ MEFs. c) proliferation curve of mutant MEFs with high and low PI3Kβ$^{KR}$ expression levels compared to that of wild-type MEFs with or without 100 nM TGX-221 treatment (TGX).

In agreement with the role of p110β in embryonic development (Bi et al., 2002), the present inventors identified two distinct groups of embryos that appeared either healthly or abnormal. The analysis of mouse embryonic fibroblast (MEFs) derived from these two mutant population revealed that the expression of PI3Kβ$^{KR}$ protein was markedly different (FIG. 3a). It was determined that normal embryos reached 50-80% of control levels of p110β expression (High) while abnormal embryos attained only 5-20% of wild-type levels (Low) (FIG. 3a).

Measurement of PI3Kβ lipid kinase activity in PI3K β$^{KR/KR(High)}$ MEFs revealed, as expected, that the enzymatic activity of the expressed mutant p110β did not increase above background (FIG. 3b), thus confirming that the mutant protein lacked its catalytic activity. Interestingly, p85-associated PI3K lipid kinase activity was not decreased, indicating that the mutation did not alter the function of other class IA PI3Ks.

Since p110β is activated downstream growth factor receptors, and cell growth is the driving force during embryonic development, the present inventors analyzed cell proliferation of PI3Kβ$^{KR/KR(High)}$, PI3Kβ$^{KR/KR(Low)}$ and PI3Kβ$^{+/+}$ MEFs. We found that the enzymatic activity of p110β is not involved cell proliferation of MEFs. Consistently, PI3K β$^{KR/KR(High)}$ and PI3Kβ$^{+/+}$ treated with p110β specific inhibitors such as TGX-221 or TGX-155 (Jackson et al., 2005; Robertson et al., 2001), whose chemical formulas is depicted in FIG. 17, showed a growth rate comparable to that of the controls (FIG. 3c). In contrast, when p110β is expressed at the low levels showed by PI3Kβ$^{KR/KR(Low)}$ MEFs, cell proliferation is significantly reduced (FIG. 3c). All these findings indicate that p110β possesses a kinase independent function, as it was already shown for another ClassI PI3K (Patrucco et al., 2004).

Example 3

Impairment of Akt/PKB Phosphorylation

Figure 4:
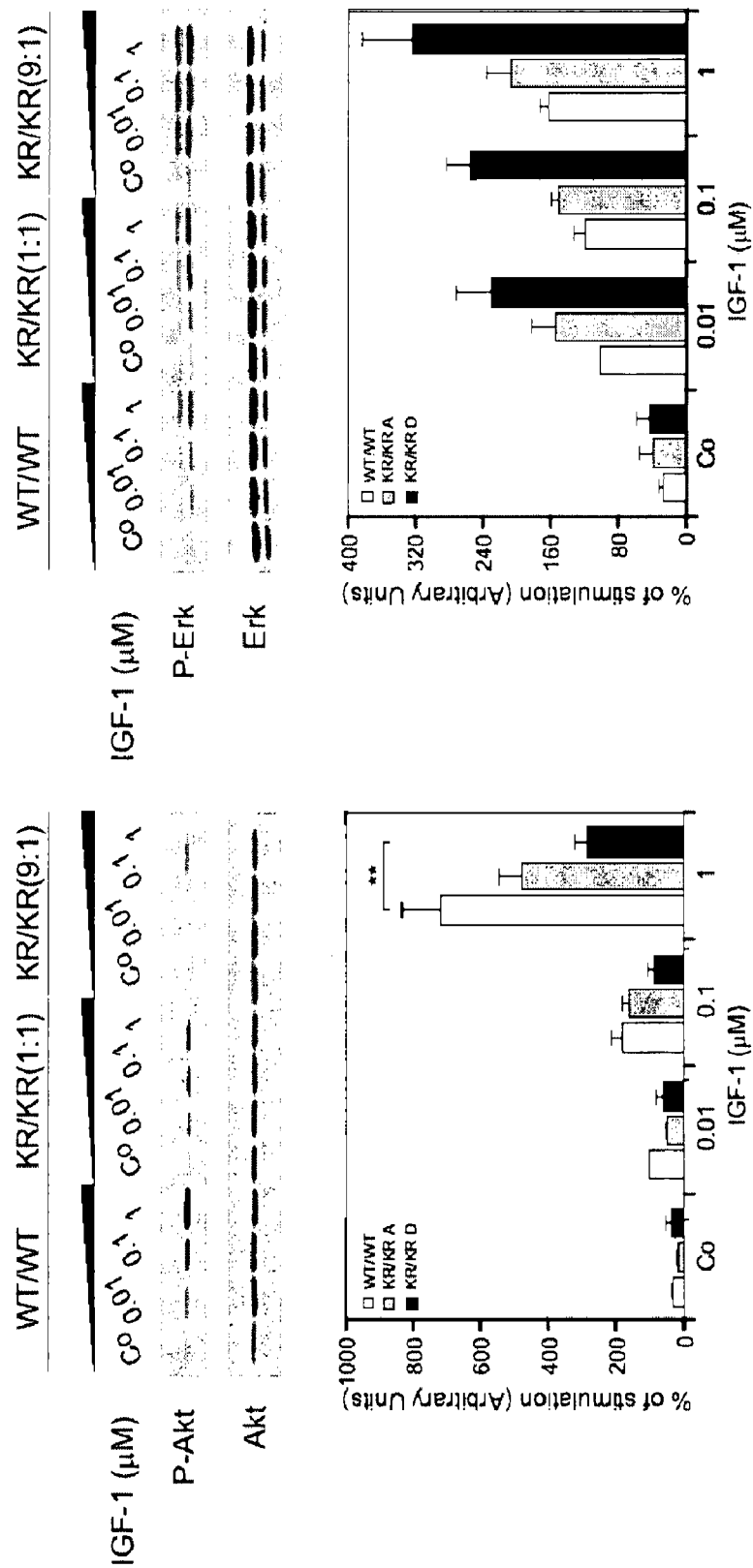
FIG. 4. Analysis of IGF-1 and insulin-dependent Akt/PKB and Erk1/2 phosphorylation in wild-type and mutant MEF. A representative blot is shown of eight independent experiments (upper panel) together with densitometric analysis (lower panel). a) Effects of IGF-1; b) Effects of insulin. WT: wild-type MEF; KR/KR A: MEF from alive embryos; KR/KR D: MEF from dead embryos.
Figure 4:
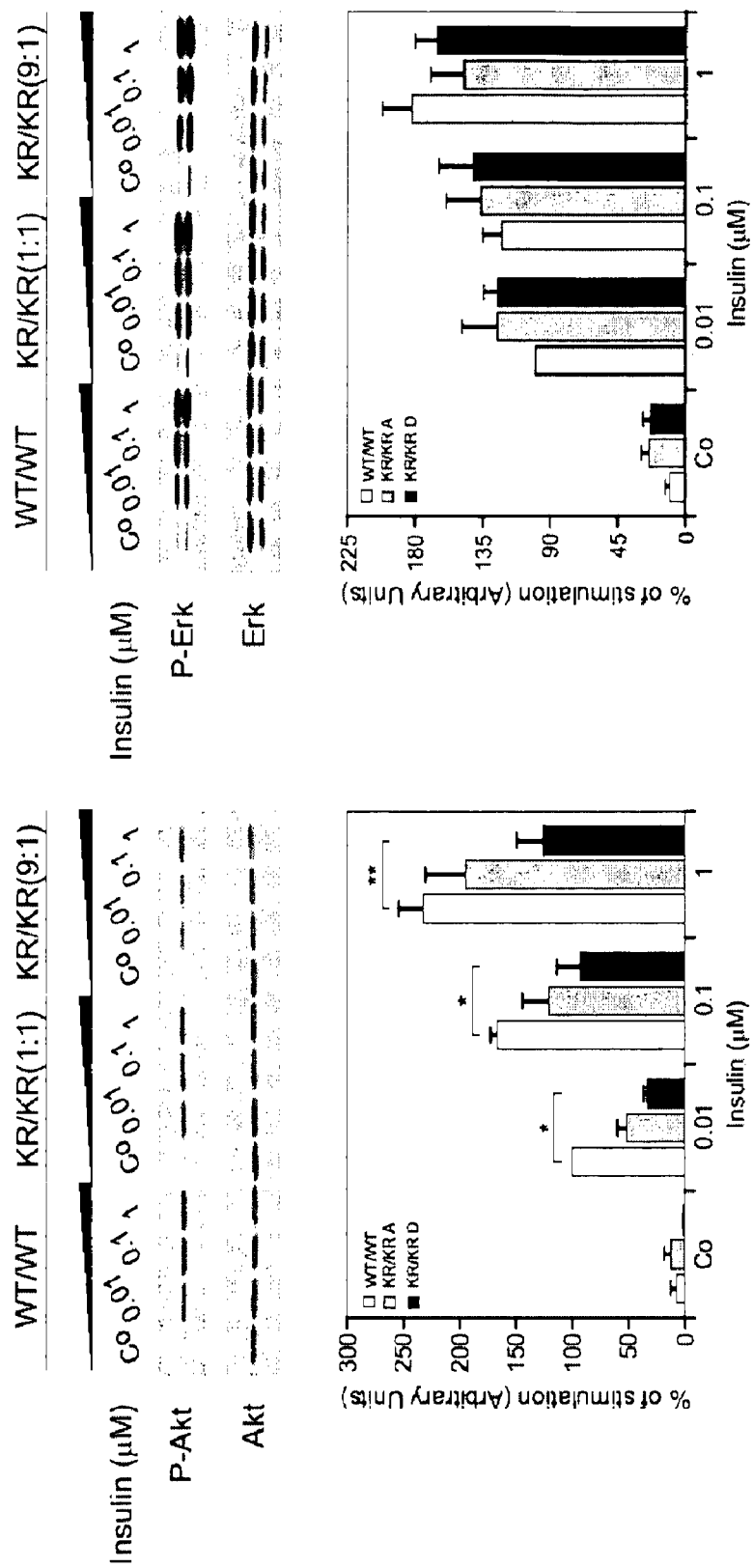

The present inventors next explored the possibility that expression of the PI3Kβ$^{KR}$ protein could be correlated with defective activation of the PI3K signaling pathway in MEFs. Previous reports suggest a specific role of PI3Kβ in mediating signalling events triggered by insulin and IGF-1 (Hooshmand-Rad et al., 2000). The effect of the mutation in fibroblasts (MEF) derived either from PI3Kβ$^{KR/KR(High)}$ and PI3Kβ$^{KR/KR(Low)}$ embryos was, therefore, analyzed following stimulation with these two agonists. IGF-1 (FIG. 4a) and insulin-mediated (FIG. 4b) phosphorylation of Akt/PKB appeared more strongly decreased in PI3Kβ$^{KR/KR(Low)}$ than in PI3Kβ$^{KR/KR(High)}$ MEFs, thus demonstrating that the kinase independent function of PI3Kβ might be required for Akt activation. In addition, accordingly to what shown in previous reports (Rommel et al., 1999), IGF-1-mediated phosphorylation of Erk1/2 was increased and this effect appeared proportional to the reduction in Akt/PKB activation (FIGS. 4a and b). On the other hand, insulin-mediated Erk1/2 phosphorylation was unaffected by the mutation (FIGS. 3a and b).

Example 4

Insulin Resistance

Figure 5:
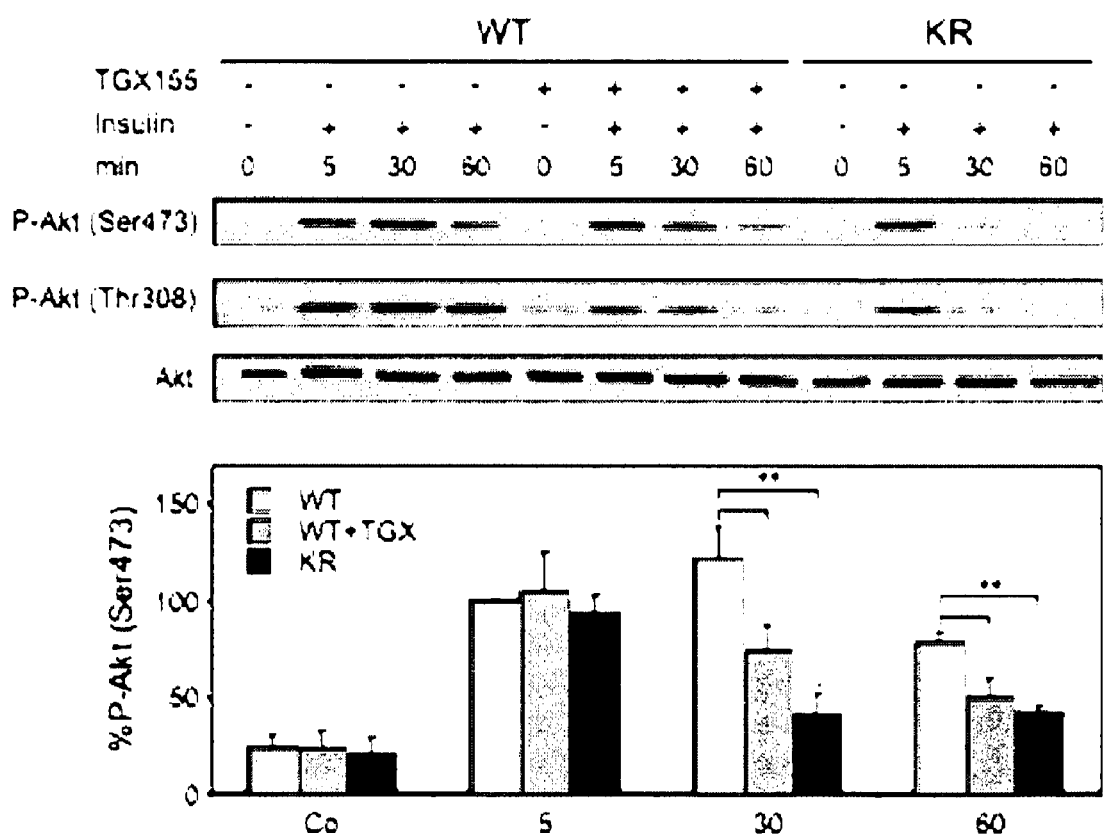
FIG. 5. After insulin stimulation, Akt phosphorylation declines in PI3Kβ$^{KR/KR}$ liver faster than controls. Phosphorylation of Erk1/2 and Akt (on Thr308 and Ser473) in livers of mice of the given genotype with and without TGX-155 treatment. Lower panel: quantification of Akt phosphorylation on Ser473 (n=5)

The reduction in insulin induced Akt/PKB phosphorylation in PI3Kβ$^{KR/KR(Low)}$ MEFs suggested that a similar effect could take place in vivo. To test this hypothesis, Akt/PKB phosphorylation was tested in wild-type and mutant mice in tissues known to be particularly sensitive to insulin signaling like the liver. In agreement with the major role of p110α in insulin signaling (Foukas et al., 2006) no differences in Akt phosphorylation were found after 5 minutes of insulin stimulation in livers from PI3Kβ$^{KR/KR}$ mice as well as wilde type mice treated with TGX-155 (FIG. 5). On the contrary, Akt activation declined significantly faster than in untreated wild-type controls (FIG. 5). These data showed that PI3Kβ is activated by the insulin receptor at later time of insulin stimulation while p110α activity is likely more rapidly inactivated (Foukas et al., 2004).

Figure 6:
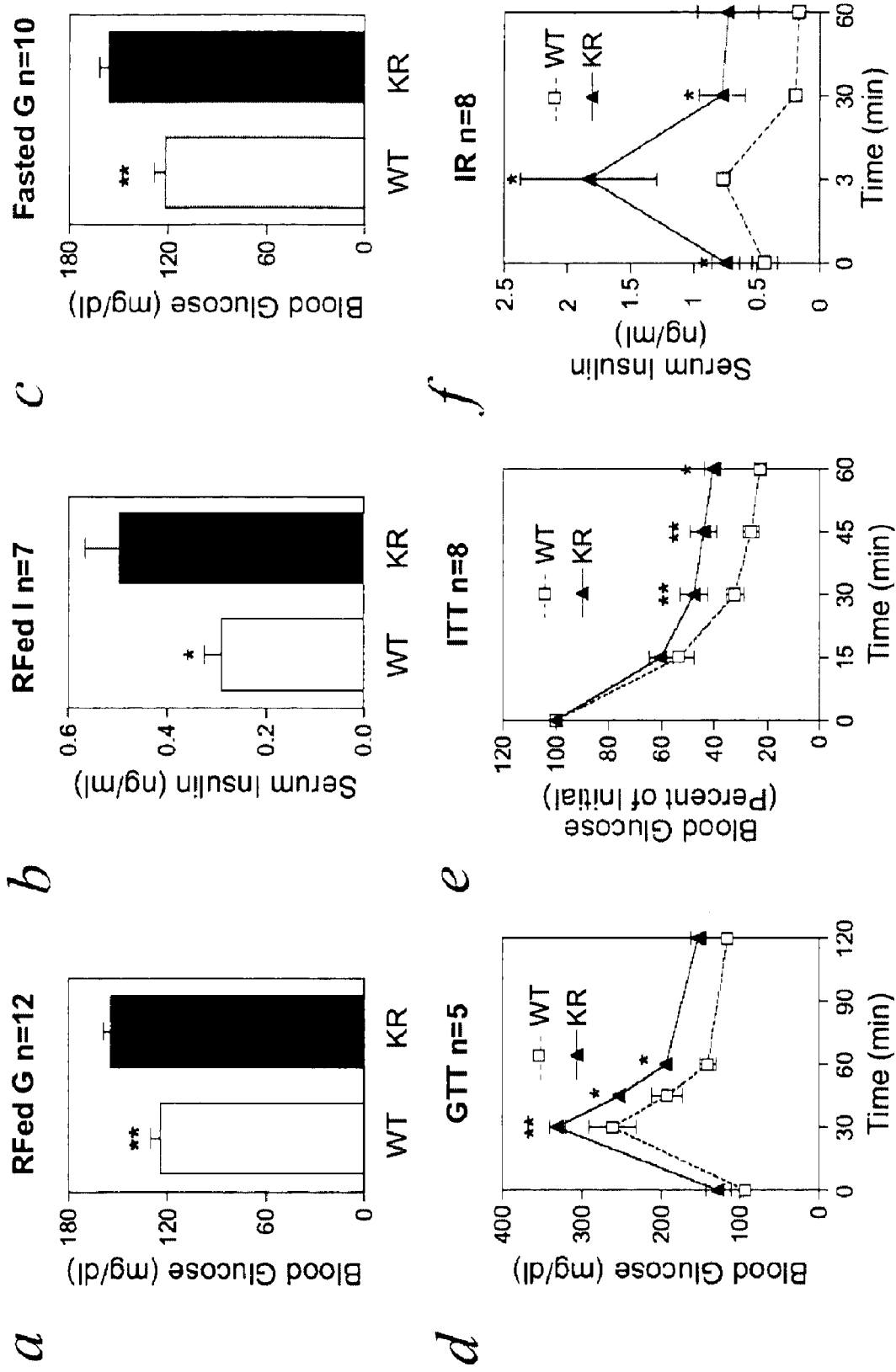
FIG. 6. Insulin-dependent glucose metabolism in 6-months old wild-type (WT) and PI3Kβ$^{KR/KR}$ mice. Plasma glucose in random fed mice (n=9 per genotype). b) Insulin levels in the plasma of random fed mice (n=9 per genotype). c) Plasma glucose in fasted mice (wild type, n=9; KR, n=11). d) Glucose tolerance test (n=5 per genotype). e) Insulin tolerance test (n=7 per genotype). f) Insulin levels in plasma of glucose treated fasted animals. * P<0.05, ** P<0.01 by Student's t or two way ANOVA followed by Bonferroni's post hoc analysis.

Reduced p110β function has been correlated with the incidence of type 2 diabetes associated with low birthweight (Ozanne et al., 2006). This suggests that mutant mice may suffer from disorders due to impaired insulin-dependent regulation of metabolism. Glucose blood levels in six months-old PI3Kβ$^{KR/KR}$ mice were 20% higher compared to wild type controls (n=7, p<0.05) either in normal conditions or after 18 hours fasting (FIGS. 6a and c). Mutant mice were found to produce about 50% more insulin than wild-type mice (see FIGS. 6b and f), thus suggesting a peripheral insulin resistance. Consistent with this view, 6 months-old PI3Kβ$^{KR/KR}$ mice showed a mild reduced response to glucose or insulin tolerance tests (FIGS. 6d and e), thus presenting a condition similar to the initial phases of human type-2 diabetes.

Example 5

Male Sterility

Figure 7:
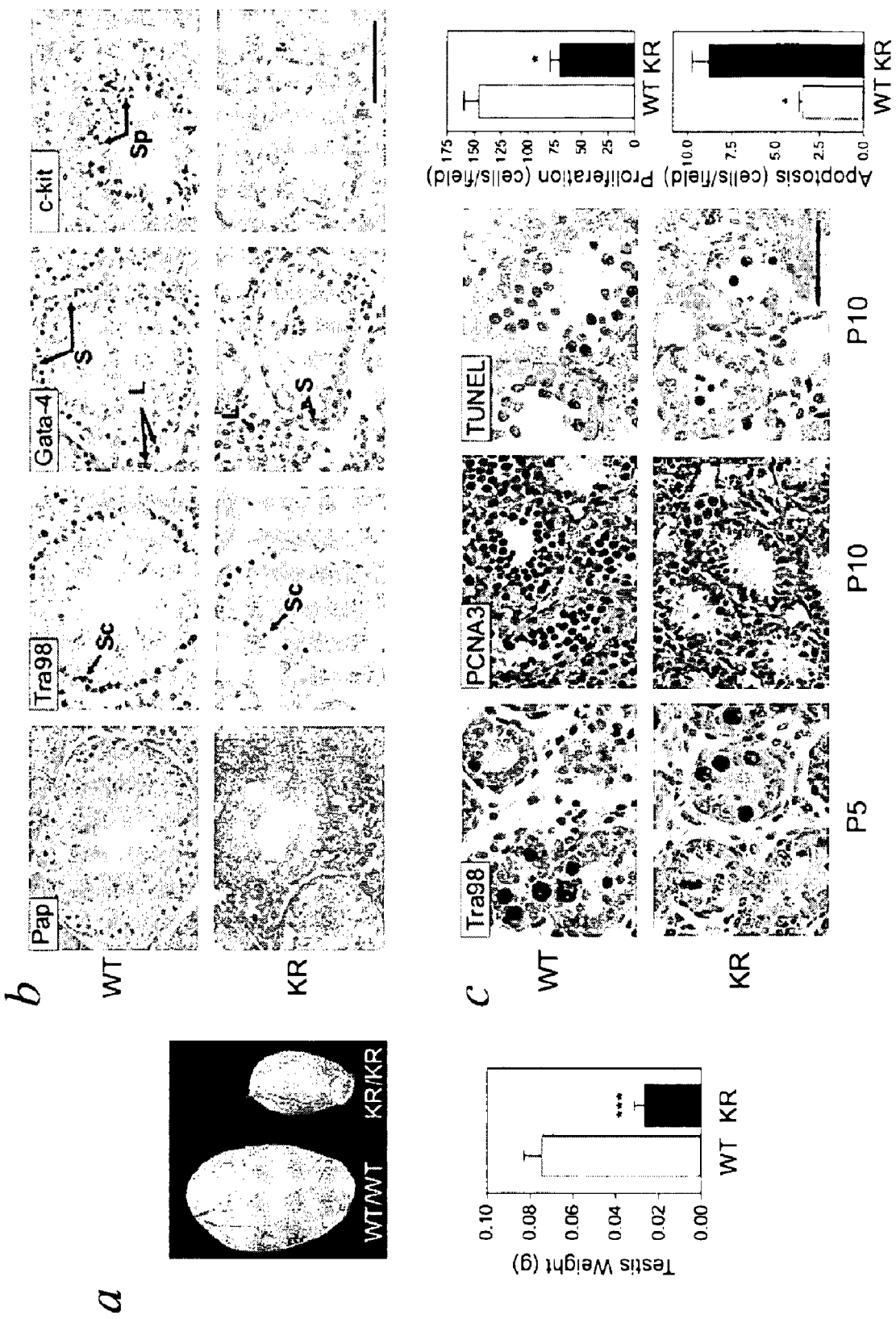
FIG. 7. Abnormal testis development in PI3Kβ$^{KR/KR}$ males. a) Analysis of testis morphology (upper panel) and of testis weight (lower panel; n=6, ***: P<0.001 by Student's T test) in wild-type (WT) and homozygous mutant (KR) 8 weeks old males. b) Histological analysis of testis of 8 weeks old mice. Sc: Spermatogonial stem cells; S: Sertoli cells; L: Leydig cells, Sp: spermatocytes. Tra98, GATA4 and c-Kit immunostaining is shown. Bar represents 100 µm. c) Histological analysis of testes at post-natal day 10. Tra98 positive primordial germ cells are equally detectable in both cell types. Proliferating cells were labelled with PCNA3 and counts were scored in 10 fields from 3 individuals. Apoptotic cells were marked by TUNEL and counted in 10 fields from 3 pups of each genotype. Bar represents 100 µm.

While PI3Kβ$^{KR/KR}$ females were fertile, homozygous males showed reduced testis size and were not able to produce spermatozoa (FIG. 7a). Histological analysis of the testes of homozygous mice revealed empty seminiferous tubules and a block in spermatogenesis (FIG. 7b). These events were the result of defective proliferation and survival of primordial germ cells (PGC): in fact, seminiferous tubules of PI3Kβ$^{KR/KR}$ mice still showed spermatogonial stem cells, indicating that PI3Kβ mutation did not affect the ability of PGCs to migrate to gonads, and Sertoli and Leydig cells were normally detected (FIG. 7c). Nonetheless, proliferation and survival of spermatogonia in testis sections at postnatal day 10 showed a 3-fold increase in apoptosis (FIG. 7c upper right) and a 2-fold decrease in proliferation (FIG. 7c lower right).

Example 6

Protection from HER-2/neu Induced Breast Cancer Development

Multiple evidences suggest that PI3Ks might be involved in tumorigenesis (Cully et al., 2006). The finding that PI3Kβ was involved in the control of proliferation and survival suggested that this particular isoform could play a role in cell proliferation, and so in tumor formation. To test this hypothesis, the effect of the functional inactivation of PI3Kβ in tumorigenesis was studied in a model of breast cancer, i.e. the mouse expressing the HER-2/neu oncogene (neuT transgene) (Boggio et al., 1998), where the genetic interaction between receptors of the HER family and PI3K is well known. Despite the therapeutic intervention with the monoclonal antibody Herceptin/trastuzumab, which blocks the said pathway is established in clinical practice, resistance to therapy is very frequent and often involves deregulation of the PI3K pathway (Nahta et al., 2006).

Figure 8:
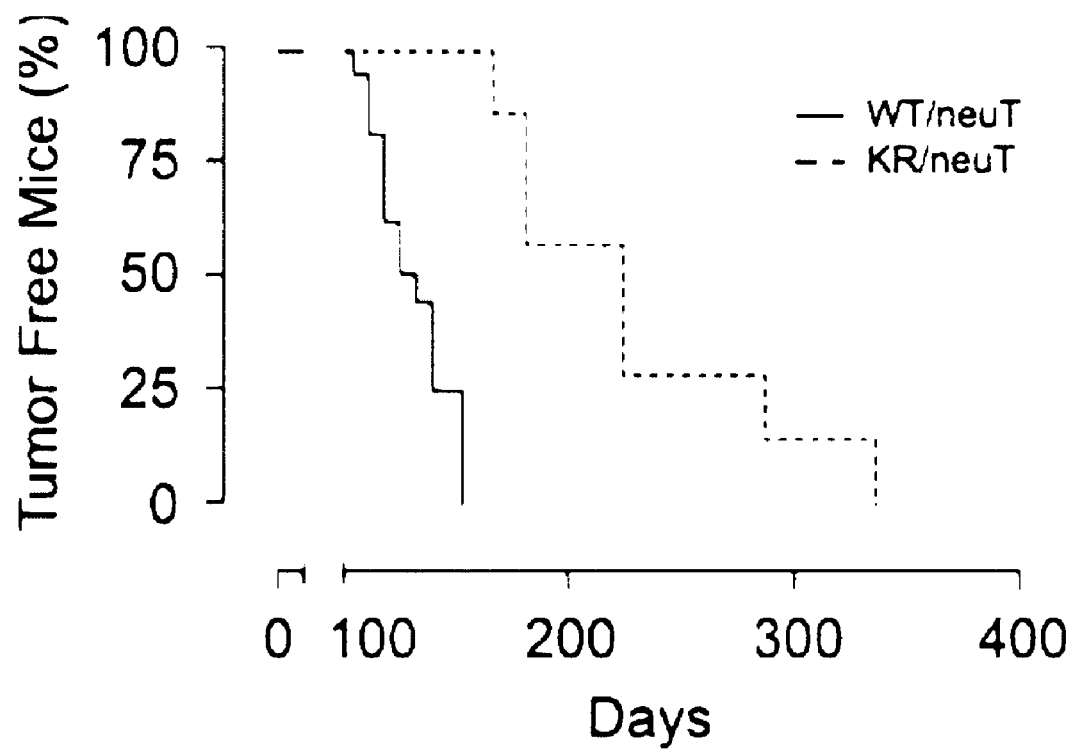
FIG. 8. Kinetics of tumor appearance in neuT/PI3Kβ$^{+/+}$ (n=16) and PI3Kβ$^{KR/KR}$ (n=7) compound mutant mice. P=0.01 by Montel-Haenszel Log-rank test.
Figure 9:
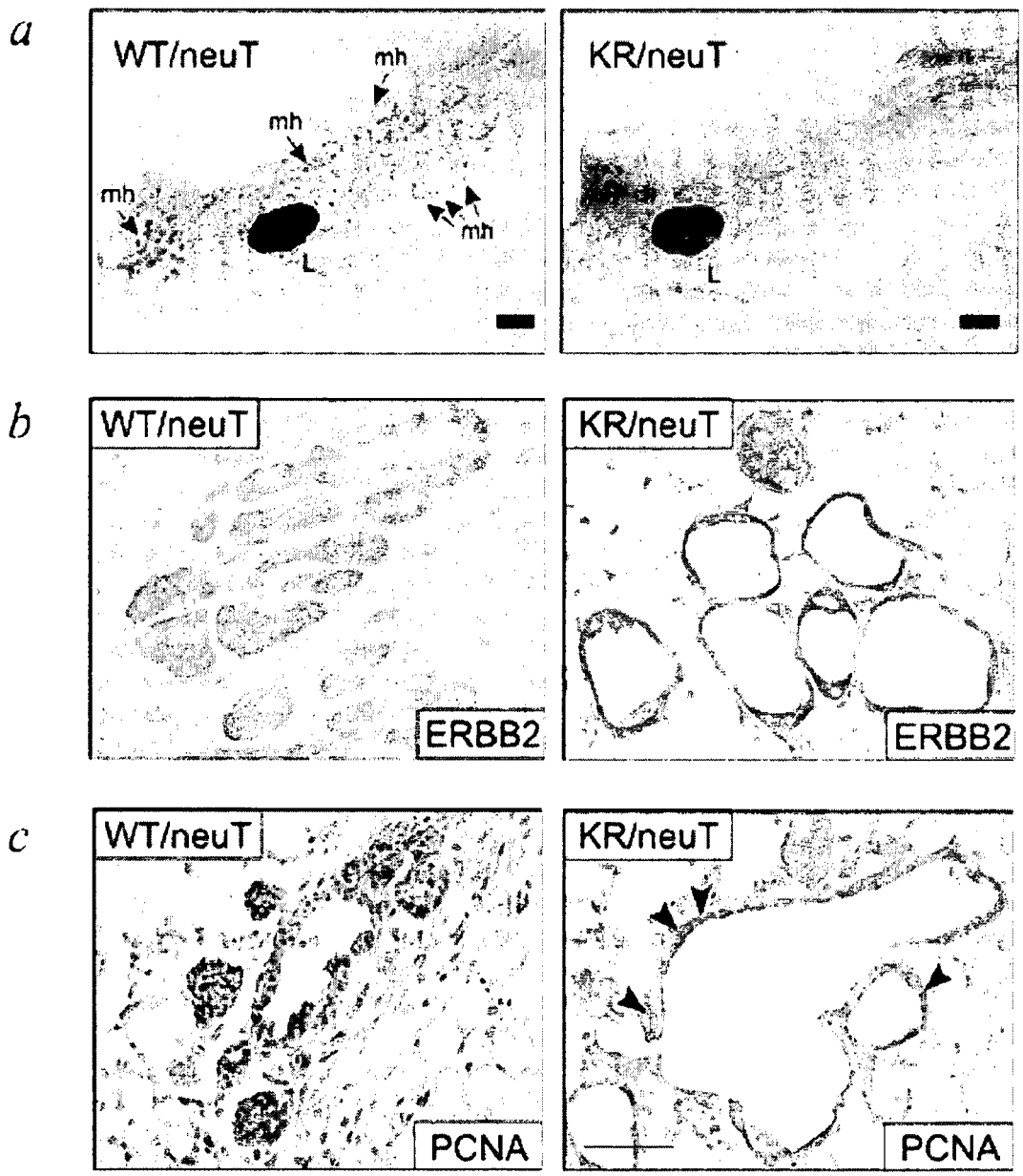
FIG. 9. Requirement of PI3Kβ for Erbb2-driven breast cancer development. a) Whole mount preparation of PI3Kβ–/–/neuT and PI3Kβ$^{KR/KR}$/neuT mammary glands at 10 weeks. PI3Kβ$^{KR/KR}$/neuT mammary gland shows a marked reduction of duct side buds constituited by atypical hyperplastic lesions and early neoplastic lesion. L: lymphonode, mh: athypical mammary hyperplastic and early neoplastic lesions. b) and c) Histology of mammary glands. Ducts were stained with anti Erbb2 (b) and with anti PCNA antibodies (c) to show transgene expression and proliferating cells, respectively. Bar represents 100 µm. Arrowheads indicte PCNA-positive cells in the mutant sample.

Mice carrying the PI3Kβ mutant allele were thus intercrossed with mice expressing the HER-2/neu oncogene, which develop breast cancer with high penetrance (Guy et al., 1992). Although cross-breedings were complicated by the infertility of mutant males, compound mutants homozygous for the PI3Kβ$^{KR}$ allele and heterozygous for the HER-2/neu oncogene were obtained. To avoid the possible bias on tumor formation of heterogeneous genetic background, studies were carried out only with mutant and control littermates obtained from heterozygous crosses. In this way, mice analyzed shared the highest genomic background possible. A cohort of 7 mutant and 16 control animals was followed for 50 weeks. PI3Kβ mutants showed a significant delay (P<0.0001) in the development of the first tumor, indicating that the identified K805R inactivating mutation of PI3β gene is protective against HER-2/neu oncogene induced cancer formation (see FIG. 8). Whole mount preparations of 10 weeks PI3Kβ$^{+/+}$/neuT and PI3Kβ$^{KR/KR}$/neuT mammary glands showed a marked reduction of duct side buds constituted by atypical hyperplastic lesions and early neoplastic lesion (FIG. 9a). Moreover, immunohistochemistry of PI3Kβ$^{+/+}$/neuT and PI3Kβ$^{KR/KR}$/neuT mammary gland ducts realed that both genotypes expressed activated Erbb2. However, while in PI3Kβ$^{+/+}$/neuT mice foci of transformation contained an high number of proliferating PCNA positive cells thus completely filling duct lumina, PI3Kβ$^{KR/KR}$/neuT mammary glands showed empty and scarcely proliferating structures (FIGS. 9b and c). In conclusion, as shown in Table 2, compound mutant mice showed a significant increase in the time required for the development of a 2 mm diameter tumor. Similarly, they showed an average period of 279±14 days to develop a 8 mm diameter tumor, a time that nearly corresponds to the average lifespan of a wild-type animal. Indeed, the growing time of the PI3Kβ$^{KR/KR}$ tumors was two-fold slower than wild-type controls.

TABLE 2

| | Latency[a] | Survival[b] | Growth[c] |
| --- | --- | --- | --- |
| neuT/PI3Kβ$^{-/-}$ | 174 ± 5 | 207 ± 17 | 33 ± 12 |
| neuT/PI3Kβ$^{KR/KR}$ | 227 ± 9 | 279 ± 14 | 52 ± 5 |
| | p < 0.0001 | p = 0.01 | p < 0.05 |

[a]time in days from the birth and the growth of a 2 mm diameter tumor
[b]time in days from the birth and the growth of a 8 mm diameter tumor
[c]time in days for a 2 mm diameter tumor to reach a 8 mm diameter tumor
Statistical analysis: Student's paired t test Overall, these data suggest that the reduction of PI3Kβ function protects from the development of HER-2 positive breast cancers and significantly delay their progression.

Example 7

Figure 10:
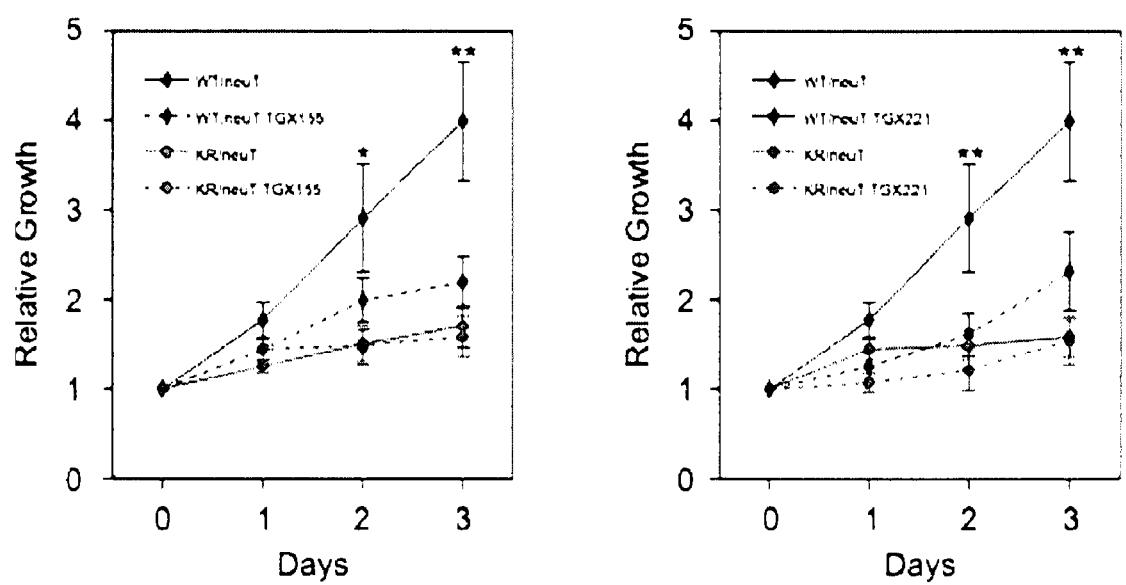
FIG. 10. Requirement of PI3Kβ for cell proliferation of tumor derived mammary gland cancer cell lines. Proliferation curves of cultured tumor cells of the two genotypes in the absence or presence of TGX-155 (10 µM) and TGX-221 (100 nM)p110β selective inhibitors. Statistical significance: wild-type cells vs all other conditions; other pairs of datasets: n.s.

Requirement of P110β Catalytic Activity for Cell Proliferation of Tumor Derived Mammary Gland Cancer Lines In agreement with what shown in vivo, in vitro tumor cell from PI3Kβ$^{KR/KR}$ mice grew significantly slower than controls (FIG. 10). Moreover, to further test if the protection against breast cancer development was intrinsic to the lack of the kinase activity, tumor cells from PI3Kβ$^{KR/KR}$ and PI3Kβ$^{+/+}$ mice were cultured in the presence of p110β selective inhibitors, TGX-155 and TGX-221. This treatment caused a significant reduction in proliferation in wild-type tumor cells, thus demonstrating that oncogenic Erbb2 drives tumor growth largely through p110β catalytic activity.

Example 8

Identification of a Test Compound that Binds to PI3Kβ Protein

The prior art discloses different systems for identifying compounds interfering with the phosphorylation activity of PI3K-related kinases, by means of antibodies specific for a moiety conjugated to the potential inhibitor (WO-A-98/

55602), the analysis of alterations in motility of cells exposed to the potential inhibitor (WO-A-99/35283), lipid extraction combined to chromatographic separation (Ward, 2000), directly labeled aminoglycosides (WO-A-00/18949), thin layer chromatography (Frew et al., 1994), or scintillation proximity assays for aminoglycoside binding molecules (WO-A-2002/101084).

Purified PI3Kβ protein comprising a glutathione-S-transferase protein and absorbed onto glutathione-derivatized wells of 96-well microtiter plates are contacted with test compounds from a small molecule library at pH 7.0 in a physiological buffer solution. PI3Kβ protein comprises an amino acid sequence shown in SEQ ID NO.: 3 or 4.

The test compounds comprise a fluorescent tag. The samples are incubated for 5 minutes to one hour. Control samples are incubated in the absence of a test compound.

The buffer solution containing the test compounds is washed from the wells.

Binding of a test compound to PI3Kβ protein is detected by fluorescence measurements of the contents of the wells. A test compound which increases the fluorescence in a well by at least 15% relative to fluorescence of a well in which a test compound was not incubated is identified as a compound which binds to PI3Kβ.

Example 9

Identification of a Test Compound which Decreases PI3Kβ mRNA Expression

A test compound (siRNA, shRNA, antisense RNA) is administered by transfection or infection to a culture of human carcinoma cells derived from breast, melanoma, prostate, colon, ovary, uterus, hepatocarcinoma and small cell lung carcinoma and incubated at 37° C. for 2 days. A culture of the same type of cells transfected/infected for the same time without the test compound provides a negative control.

Transfection and infection are performed using a standard procedure with commercially available kits.

RNA is isolated from the two cultures as described in Chozminski and Sacchi. Northern blots are prepared as described in Maniatis and hybridized with $^{32}$P-labeled human PI3Kβ-specific probe. The probe comprises at least 300 contiguous nucleotides selected from the complement of SEQ ID NO.:1. A test compound which decreases the PI3K-specific signal relative to the signal obtained in the absence of the test compound is identified as an inhibitor of PI3Kβ gene expression.

Example 10

Identification of a Test Compound which Decreases PI3Kβ Protein Expression

A test compound (siRNA, shRNA, antisense RNA) is administered by trasfection/infection to a culture of human carcinoma cells derived from breast, melanoma, prostate, colon, ovary, uterus, hepatocarcinoma and small cell lung carcinoma and incubated at 37° C. for 10 to 45 minutes. A culture of the same type of cells transfected/infected for the same time without the test compound provides a negative control.

Transfection and infection are performed using a standard procedure with commercially available kits.

Cells will be extracted with 1% NP-40 lysis buffer (1% NP-40, 150 mM NaCl, 50 mM Tris-HCl pH 8.5 mM EDTA, mM NaF, 10 mM $Na_4P_2O_7$, 0.4 mM $Na_3VO_4$, 10 μg/ml leupeptin, 4 μg/ml pepstatin and 0.1 unit/ml aprotinin). Cell lysates are centrifuged at 13.000×g for 10 min and the supernatants are collected and assayed for protein concentration with the Bio-Rad protein assay method. Proteins are run on SDS-PAGE under reducing conditions. Following SDS-PAGE, proteins are transferred to nitrocellulose, incubated with specific antibodies and then detected with peroxidase-conjugate secondary antibodies and chemoluminescent ECL reagent.

Example 11

Production of Viral Particles Containing siRNA Sequences for PI3Kβ Down-regulation A viral particle which inhibits PI3Kβ expression is administered by infection to a culture of human carcinoma cells derived from breast, melanoma, prostate, colon, ovary, uterus, hepatocarcinoma and small cell lung carcinoma. A culture of the same type of cells infected for the same time with a viral particle that does not interfere with PI3Kβ expression provides a negative control.

Human or mouse PI3Kβ shRNA and PI3Kβ unrelated controls inserted in suitable retro or lenti-viral vectors are purchased from commercial sources (for example from Open Biosystems, 6705 Odyssey Drive, Huntsville, Ala. 35806, USA). Virus titers are assessed by transducing HeLa cells with serial dilutions of viral stocks. Aliquots of virus, plus 8 microgram/ml of polybrene (Sigma), are used to infect exponentially growing tumour cells ($1 \times 10^5$/ml). Fresh medium is supplemented at 24 hours after the infection. Cells infected with pSRG retroviruses are enriched by selection with puromycin (1 microgram/ml, for 7 days).

Example 12

Exemplary Functional Assays: Apoptosis

A test compound which reduces PI3Kβ expression and blocks PI3Kβ kinase activity and/or PI3Kβ function is administered at scalar doses to a culture of human carcinoma cells derived from breast, melanoma, prostate, colon, ovary, uterus, hepatocarcinoma and small cell lung carcinoma and incubated at 37° C. for 2 days. A culture of the same type of cells treated for the same time without the test compound provides a negative control.

Cells are plated on glass coverslips and fixed in 4% paraformaldehyde for 10 min at room temperature in a 24-well plate. The In Situ Cell Death Detection kit (Roche Applied Science) is used to identify apoptotic nuclei within the cell culture according to the manufacturer's protocol. Briefly, cells are rinsed three times in PBS and 50 microliters of TUNEL reaction mixture is added to each well. Cells are incubated in the dark for 60 minutes at 37° C. and then washed three times 5 minutes each with PBS. In the first washing Hoechst staining is added to label all the nuclei. Ten random fields per section will be documented by photomicroscopy, and the percentage of TUNEL positive epithelial cell nuclei relative to the total number of the epithelial cell nuclei.

Example 13

Exemplary Functional Assays: Cell Cycle Progression

A test compound which reduces PI3Kβ expression and blocks PI3Kβ kinase activity and/or PI3Kβ function is administered at scalar doses to a culture of human carcinoma cells derived from breast, melanoma, prostate, colon, ovary, uterus, hepatocarcinoma and small cell lung carcinoma and incubated at 37° C. for 2 days. A culture of the same type of cells treated for the same time without the test compound provides a negative control.

Actively growing cells are pulsed in a tissue culture flask for one hour with 10 µM BrdU (Sigma, Cat. No. B5002). Cells are detached and poured into a centrifuge tube and centrifuged 10 minutes at 400×g at RT. Pellet is resuspended by tapping tube and ice cold 70% ethanol to cells is added dropwise, to a final concentration of $1\times10^6$ cells/100 µl. Incubate 20 minutes at RT, aliquot 100 µl into each test tube (12 mm×75 mm) and centrifuge 5 minutes. Resuspend pellet in denaturing solution and incubate 20 minutes at RT. Add 1 ml wash buffer. Mix well. Centrifuge 5 minutes. Resuspend pellet in 0.5 ml 0.1 M sodium borate ($Na_2B_4O_7$), pH 8.5, to neutralize any residual acid. Incubate 2 minutes at RT. Add 1 ml wash buffer. Mix well. Centrifuge 5 minutes. Add primary anti-BrdU monoclonal antibody (Pharmingen) in dilution buffer, Incubate 20 minutes at RT. Add 1 ml wash buffer. Mix well. Centrifuge 5 minutes. Aspirate supernatant. Add secondary antibody: dilute FITC-conjugated goat anti-mouse Ig (PharMingen Cat. No. 12064D) in dilution buffer, such that 50 µl contains the optimal concentration. Resuspend cell pellet in 50 µl of the diluted antibody. Incubate 20 minutes at RT. Add 1 ml wash buffer. Mix well. Centrifuge 5 minutes. Aspirate supernatant. Resuspend pellet in 0.5 ml propidium iodide (10 µg/ml in PBS). Incubate 30 minutes at RT, protected from light. Analyze the cells by flow cytometry, exciting at 488 nm and measuring the BrdU-linked green fluorescence (FITC) through a 514 nm bandpass filter and the DNS linked red fluorescence (PI) through a 600 nm wave-length filter. Following analysis, flush flow cytometer for 10 minutes with 10% bleach and 5 minutes with $dH_2O$.

Example 14

Exemplary Functional Assays: Migration

A test compound which reduces PI3Kβ expression and blocks PI3Kβ kinase activity and/or PI3Kβ function is administered at scalar doses to a culture of human carcinoma cells derived from breast, melanoma, prostate, colon, ovary, uterus, hepatocarcinoma and small cell lung carcinoma and incubated at 37° C. for 2 days. A culture of the same type of cells treated for the same time without the test compound provides a negative control.

For migration assays, the lower side of Transwell chambers (Costar) are coated with 10 microgram/ml of fibronectin. $5\times10^4$ cells are seeded on the upper side of the filters and incubated in RPMI medium (Gibco) in the presence of 25 U/ml HGF (Sigma) in the bottom wells of the chambers. After 2 hours cells on the upper side of the filters are mechanically removed. Cells migrated to the lower side are fixed and stained with Diff-Quick kit and counted.

Example 15

Exemplary Functional Assays: Invasion

A test compound which reduces PI3Kβ expression and blocks PI3Kβ kinase activity and/or PI3Kβ function is administered at scalar doses to a culture of human carcinoma cells derived from breast, melanoma, prostate, colon, ovary, uterus, hepatocarcinoma and small cell lung carcinoma and incubated at 37° C. for 2 days. A culture of the same type of cells treated for the same time without the test compound provides a negative control.

For invasion assays the upper of Transwell chambers (Costar) are coated with 100 microliters of Matrigel matrix basement (Becton Dickinson) diluted 1:3 in RPMI medium. $5\times10^4$ cells are seeded on the upper side of the filters and let to invade and incubated in RPMI medium (Gibco) in the presence of 25 U/ml HGF (Sigma) in the bottom wells of the chambers. Cells were left to invade for 24 or 48 hours and stained with Diff-Quick kit and counted.

Example 16

Exemplary Functional Assays:
Anchorage-independent Growth

A test compound which reduces PI3Kβ expression and blocks PI3Kβ kinase activity and/or PI3Kβ function is administered at scalar doses to a culture of human carcinoma cells derived from breast, melanoma, prostate, colon, ovary, uterus, hepatocarcinoma and small cell lung carcinoma and incubated at 37° C. for 2 days. A culture of the same type of cells treated for the same time without the test compound provides a negative control.

For anchorage-independent assays $20\times10^4$ cells are plated in 6 cm dishes in Basal layer containing 4 ml/dish of 1.2% agar (Difco) in DMEM+antibiotics+10% FBS with the following procedure. Basal layers are incubated for 16-24 hrs at 37° C. in 5% $CO_2$. 1.5 ml/dish of Top layer consisting of 0.3% agar in DMEM+antibiotics+10% FBS. Cells are incubated for 17-21 days at 37° C.

Example 17

Exemplary Activity Assays

The following assays are employed to find those compounds demonstrating the optimal degree of the desired activity The following ELISA assay (Enzyme-Linked Immunosorbent Sandwich Assay—Voller, et al., 1980, "Enzyme-Linked Immunosorbent Assay," Manual of Clinical Immunology, 2ded., Rose and Friedman, Am. Soc. Of Microbiology, Washington, D.C., pp. 359-371) may be used to determine the level of activity and effect of the different compounds on the PI3Kβ activity.

The general procedure is as follows: a compound is introduced to cells expressing PI3Kβ, either naturally or recombinantly, for a selected period of time after which, if PI3Kβ is a receptor, a ligand known to activate the receptor is added. The cells are lysed and the lysate is transferred to the wells of an ELISA plate previously coated with a specific antibody recognizing the substrate of the enzymatic phosphorylation reaction.

Non-substrate components of the cell lysate are washed away and the amount of phosphorylation on the substrate is detected with an antibody specifically recognizing phosphotyrosine compared with control cells that were not contacted with a test compound.

Other assays known in the art can measure the amount of DNA made in response to activation of a PI3Kβ, which is a general measure of a proliferative response. The general procedure for this assay is as follows: a compound is introduced to cells expressing PI3Kβ, either naturally or recombinantly, for a selected period of time after which, if PI3Kβ is a receptor, a ligand known to activate the receptor is added.

After incubation at least overnight, a DNA labeling reagent such as 5-bromodeoxyuridine (BrdU) or H3-thymidine is added.

The amount of labeled DNA is detected with either an anti BrdU antibody or by measuring radioactivity and is compared to control cells not contacted with a test compound.

Example 18

Exemplary Activity Assays: Brdu Incorporation Assays

The following assay uses cells engineered to express PI3Kβ and then evaluate the effect of a compound of interest on the activity of ligand-induced DNA synthesis by determining BrdU incorporation into the DNA.

The following materials, reagents and procedure are general to each of the following BrdU incorporation assays.

Materials and Reagents:
1. The appropriate ligand.
2. The appropriate engineered cells.
3. BrdU Labeling Reagent: 10 mM, in PBS (pH 7.4) (Boehringer Mannheim, Germany).
4. FixDenat: fixation solution (ready to use) (Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehringer Mannheim, Germany).
7. PBS WashingSolution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration=10 uM) for 1.5 hours.
5. After incubation with labeling reagent, the medium is removed by decanting and tapping the inverted plate on a paper towel. FixDenat solution is added (50 ul/well) and the plates are incubated at room temperature for 45 minutes on a plate shaker.
6. The FixDenat solution is thoroughly removed by decanting and tapping the inverted plate on a paper towel. Milk is added (5% dehydrated milk in PBS, 200 ul/well) as a blocking solution and the plate is incubated for 30 minutes at room temperature on a plate shaker.
7. The blocking solution is removed by decanting and the wells are washed once with PBS. Anti-BrdU-POD:solution (1:200 dilution in PBS, 1% BSA) is added (50 ul/well) and the plate is incubated for 90 minutes at room temperature on a plate shaker.
8. The antibody conjugate is thoroughly removed by decanting and rinsing the wells 5 times with PBS, and the plate is dried by inverting and tapping on a paper towel.
9. TMB substrate solution is added (100 ul/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

Example 19

PI3Kβ Inhibition

Inhibition of PI3Kβ function, according to the present invention, is determined in fibroblast cells (in vivo, in vitro, or ex vivo) or a suitable fibroblast cell surrogate. For in vitro assays, PI3Kβ can be recombinantly produced, for example using baculovirus, with or without peptidic tags.

In one embodiment, the PI3Kβ function inhibited is PI3Kβ-dependant phosphorylation (i.e. lipid or protein kinase activity).

Lipid kinase activity can be assessed by determining PI3Kβ-dependant phosphorylation of an endogenous substrate such as phosphatidylinositol (4,5)bisphosphate or by phosphorylation of an exogenously added substrate. An exogenously added substrate can be a natural substrate or an artificial substrate. Optionally, phosphorylation of a substrate is measured at a position D3 of the inositol ring of phosphoinositides. The general procedure for this assay is as follows: fibroblast cells or a suitable fibroblast cells surrogate are incubated, in the presence or absence of inhibitors, with either IGF-1 or insulin or other agonists known to activate PI3Kβ. To immunoprecipitate PI3Kβ with anti-PI3Kβ antibodies, cells are washed with ice cold PBS and lysed with a buffer containing Tris-HCl 20 mM, NaCl 138 mM, KCl 2.7 mM, pH8 supplemented with 5% glycerol, 1 mM $MgCl_2$, 1 mM $CaCl_2$, 1 mM sodium-o-vanadate, leupeptin, pepstatin, 1% NP40, 5 mM EDTA, 20 mM NaF. Lysates are centrifuged at 15'000 rpm for 10' (4° C.) and the cleared extract is removed to a new tube. Protein extracts are pre-clear with sepharose prot A or G for 1 h. Supernatant is transferred in a new tube and anti PI3Kβ antibody and sepharose prot A or G are added and incubated for 2 h at 4° C. Sepharose beads are sedimented by centrifugation and supernatant is removed. Sepharose beads are washed twice with washing buffer containing 0.1M Tris-HCl, pH 7.4, 0.5M LiCl and twice with kinase buffer containing 20 mM HEPES, pH 7.4, 5 mM $MgCl_2$. The pellet (immunoprecipitate) is vacuum-dried and resuspended in 40 µl of kinase buffer. Phosphatidylserine (PS) 1 mg/ml in $CHCl_3$/MetOH (9:1) and Phosphatidylinositol (PI) 1 mg/ml in $CHCl_3$/MetOH (2:1) are mixed in a PS/PI substrate solution A containing: 300 µg PS+300 µg PI that are dried with nitrogen, resuspended in 300 µl of kinase buffer and sonicated. 10 µl of substrate solution A and 10 µl of substrate solution B (ATP cold 0.06 mM+$^{32}$P-ATP 5 µCi per reaction+kinase buffer) are added to the immunoprecipitate. The kinase reaction is carried out at 30° C. for 10' with vigorous mixing. The reaction is stopped by addition of 100 µl of HCl 1N. Lipids are extracted by addition of 200 µl of $CHCl_3$/MetOH 1:1. After vigorous mixing and centrifugation for 4' at 3'000 rpm, the organic phase (phase below) is collected and lipids are dried in speed vac for 30'. Phosphoinositides are separated by thin layer chromatography (TLC).

TLC plates are dehydrated in microwave. Dried lipids are resuspended in 40 µl (20 µl+20 µl) CHCl$_3$/MetOH (2:1) and applied dropwise with an Hamilton glass syringe on the TLC plate. The plates are air dried for 5-10', developed in a CHCl$_3$/MetoH/H$_2$O/NH$_4$OH in a gas-chromatography chamber and exposed to radiographic films.

Optionally, the phosphorylated residue is a serine or threonine residue of a peptidic substrate.

By way of a non-limiting example, PI3Kβ phosphorylation is determined by using an antibody that is specific for PI3Kβ having phosphorylated serine.

By way of non-limiting example, PI3Kβ-dependant phosphorylation can be measured in accordance with this invention by an in vitro kinase assay. In this assay, PI3Kβ-dependant phosphorylation is determined by measuring the ability of PI3Kβ to incorporate a phosphate into a substrate. Optionally, the phosphate is labeled. Optionally, the phosphate is radiolabeled.

PI3Kβ-dependant phosphorylation can also be measured using gamma-P labeled ATP as set forth, by way of example, in Example 4 of WO 98/35016.

In another example, PI3Kβ-dependent phosphorylation can be measured by using antibody specific for phosphorylated PKB/Akt protein at threonine308 or serine473. The amount of antibody specific for phosphorylated PKB/Akt (visualized, for example, by Western Blot) can be normalized to the amount of antibody specific for PKB/Akt (i.e., antibody that immunoreacts with phosphorylated and non phosphorylated PKB/Akt).

PI3Kβ-dependant phosphorylation can also be measured in accordance with this invention by determining labeled phosphate incorporation into an exogenously added substrate. A potential PI3Kβ inhibitor and an endogenous PI3Kβ substrate are added to PI3Kβ, and incorporation is quantified in the presence and absence of the putative PI3Kβ inhibitor. In this embodiment, PI3Kβ can be recombinant, from a natural (mammalian source), or provided in an intact or a disrupted sf9 cell.

PI3Kβ Pseudosubstrate

In another embodiment, PI3Kβ-dependant phosphorylation (or inhibition thereof) can be quantified using an exogenous substrate comprising a PI3Kβ pseudosubstrate. A PI3Kβ pseudosubstrate can contain any modification such as, by non-limiting example, biotin.

An assay of this kind can be conducted by incubating a putative PI3Kβ inhibitor with PI3Kβ pseudosubstrate and PI3Kβ. PI3Kβ can be recombinant, from a natural (mammalian source), or provided in an intact or a disrupted sf9 cell.

PI3Kβ Pseudoenzyme

In one embodiment, recombinant PI3Kβ is a peptide comprising PI3Kβ kinase domain corresponding to PI3Kβ amino acid residues 707-1030 ("PI3Kβ pseudo-enzyme").

The PI3Kβ pseudoenzyme can further comprise an N-terminal His-Tag. PI3Kβ pseudo-enzyme can be expressed in baculovirus. The PI3Kβ pseudo-enzyme can be purified using affinity and/or conventional chromatography.

By way of a non-limiting example, PI3Kβ inhibition can be measured by detecting PI3Kβ lipid kinase activity in a lipid kinase assay.

Naturally, while the principle of the invention remains the same, the details of construction and the embodiments may widely vary with respect to what has been described and illustrated purely by way of example, without departing from the scope of the present invention as defined in the appended claims.

BIBLIOGRAPHY

Bi, L., Okabe, I., Bernard, D. J., and Nussbaum, R. L. (2002). Early embryonic lethality in mice deficient in the p110beta catalytic subunit of PI 3-kinase. Mamm Genome 13, 169-172.

Boggio, K., Nicoletti, G., Di Carlo, E., Cavallo, F., Landuzzi, L., Melani, C., Giovarelli, M., Rossi, I., Nanni, P., De Giovanni, C., et al. (1998). Interleukin 12-mediated prevention of spontaneous mammary adenocarcinomas in two lines of Her-2/neu transgenic mice. J Exp Med 188, 589-596.

Cully, M., You, H., Levine, A. J., and Mak, T. W. (2006). Beyond PTEN mutations: the PI3K pathway as an integrator of multiple inputs during tumorigenesis. Nat Rev Cancer 6, 184-192.

Foukas, L. C., Beeton, C. A., Jensen, J., Phillips, W. A., and Shepherd, P. R. (2004). Regulation of phosphoinositide 3-kinase by its intrinsic serine kinase activity in vivo. Mol Cell Biol 24, 966-975.

Foukas, L. C., Claret, M., Pearce, W., Okkenhaug, K., Meek, S., Peskett, E., Sancho, S., Smith, A. J., Withers, D. J., and Vanhaesebroeck, B. (2006). Critical role for the p110alpha phosphoinositide-3-0H kinase in growth and metabolic regulation. Nature 441, 366-370.

Guy, C. T., Webster, M. A., Schaller, M., Parsons, T. J., Cardiff, R. D., and Muller, W. J. (1992). Expression of the neu protooncogene in the mammary epithelium of transgenic mice induces metastatic disease. Proc Natl Acad Sci USA 89, 10578-10582.

Hooshmand-Rad, R., Hajkova, L., Klint, P., Karlsson, R., Vanhaesebroeck, B., Claesson-Welsh, L., and Heldin, C. H. (2000). The PI 3-kinase isoforms p110(alpha) and p110(beta) have differential roles in PDGF— and insulin-mediated signaling. J Cell Sci 113 Pt 2, 207-214.

Jackson, S. P., Schoenwaelder, S. M., Goncalves, I., Nesbitt, W. S., Yap, C. L., Wright, C. E., Kenche, V., Anderson, K. E., Dopheide, S. M., Yuan, Y., et al. (2005). PI 3-kinase p110beta: a new target for antithrombotic therapy. Nat Med 11, 507-514.

Lawlor, M. A., Mora, A., Ashby, P. R., Williams, M. R., Murray-Tait, V., Malone, L., Prescott, A. R., Lucocq, J. M., and Alessi, D. R. (2002). Essential role of PDK1 in regulating cell size and development in mice. Embo J 21, 3728-3738.

Nahta, R., Yu, D., Hung, M. C., Hortobagyi, G. N., and Esteva, F. J. (2006). Mechanisms of Disease: understanding resistance to HER2-targeted therapy in human breast cancer. Nat Clin Pract Oncol 3, 269-280.

Ozanne, S. E., Jensen, C. B., Tingey, K. J., Martin-Gronert, M. S., Grunnet, L., Brons, C., Storgaard, H., and Vaag, A. A. (2006). Decreased protein levels of key insulin signalling molecules in adipose tissue from young men with a low birthweight: potential link to increased risk of diabetes? Diabetologia 49, 2993-2999.

Patrucco, E., Notte, A., Barberis, L., Selvetella, G., Maffei, A., Brancaccio, M., Marengo, S., Russo, G., Azzolino, O., Rybalkin, S. D., et al. (2004). PI3Kgamma modulates the cardiac response to chronic pressure overload by distinct kinase-dependent and -independent effects. Cell 118, 375-387.

Robertson, A. D., Jackson, S., Kenche, V., Yaip, C., Parbaharan, H., and Thompson, P. (2001). Preparation and formulation of morpholino-substituted heterocycles as phosphoinositide 3-kinase inhibitors for therapeutic use.

Rommel, C., Clarke, B. A., Zimmermann, S., Nunez, L., Rossman, R., Reid, K., Moelling, K., Yancopoulos, G. D., and Glass, D. J. (1999). Differentiation stage-specific inhibition of the Raf-MEK-ERK pathway by Akt. Science 286, 1738-1741.

Vanhaesebroeck, B., Leevers, S. J., Ahmadi, K., Timms, J., Katso, R., Driscoll, P. C., Woscholski, R., Parker, P. J., and Waterfield, M. D. (2001). Synthesis and function of 3-phosphorylated inositol lipids. Annu Rev Biochem 70, 535-602.

Vivanco, I., and Sawyers, C. L. (2002). The phosphatidylinositol 3-Kinase AKT pathway in human cancer. Nat Rev Cancer 2, 489-501.

Wymann, M. P., Bulgarelli-Leva, G., Zvelebil, M. J., Pirola, L., Vanhaesebroeck, B., Waterfield, M. D., and Panayotou, G. (1996). Wortmannin inactivates phosphoinositide 3-kinase by covalent modification of Lys-802, a residue involved in the phosphate transfer reaction. Mol Cell Biol 16, 1722-1733.

The invention claimed is:

1. A method for screening of a pharmacologically active agent for the treatment of a HER2-positive breast cancer using (i) a polynucleotide encoding at least a portion of PI3Kβ protein or at least a portion of P110β catalytic subunit of PI3Kβ protein, or (ii) a polypeptide comprising at least a portion of PI3Kβ protein or at least a portion of p110β catalytic subunit of PI3Kβ protein; the method comprising: assaying one or more test compounds with said polynucleotide or polypeptide to select those which bind to or modulate the expression/function of PI3Kβ protein as said pharmacologically active agent, wherein said pharmacologically active agent down-regulates catalytic activity, function, stability and/or expression of PI3Kβ protein or down-regulates catalytic activity, function, stability and/or expression of p110β catalytic subunit of PI3Kβ protein; and wherein said pharmacologically active agent is a PI3Kβ inhibitor and/or antagonist.

2. The method according to claim 1, wherein said pharmacologically active agent is selected from the group consisting of small molecule inhibitors, aptamers, antisense nucleotides, RNA-based inhibitors, siRNAs, antibodies, peptides, and dominant negative proteins.

3. The method according to claim 1, wherein said pharmacologically active agent binds to at least a portion of PI3Kβ protein or at least a portion of p110β catalytic subunit of PI3Kβ protein.

4. A method for detecting the ability of a test agent to act as an antagonist or inhibitor of PI3Kβ protein useful for treatment of a HER2-positive breast cancer, the method comprising:
  (a) putting in contact a test agent with PI3Kβ protein or a fragment thereof, or cells expressing said PI3Kβ protein or a fragment thereof;
  (b) measuring PI3Kβ protein activity, function, stability, and/or expression; and
  (c) selecting the agent that reduces PI3Kβ protein activity, function, stability, and/or expression, wherein said selected agent is useful in treatment of a HER2-positive breast cancer.

5. The method according to claim 4, wherein (a) comprises putting in contact a test agent with PI3Kβ protein or a fragment thereof, or cells expressing said PI3Kβ protein or fragment thereof in presence of a suitable endogenous and/or exogenous substrate for PI3Kβ protein.

6. The method according to claim 5, wherein said substrate is phosphatidyl inositol.

7. The method according to claim 4, wherein (b) comprises measuring cell signalling, cell survival, cell proliferation, and/or phosphorylation of the substrate.

8. The method according to claim 1, wherein said polypeptide comprises residues 707-1030 of SEQ ID NO: 3.

9. The method according to claim 4, wherein said fragment comprises p1101β catalytic subunit of PI3Kβ protein.

* * * * *

SEQUENCE LISTING

```
<160> NUMBER OF SEQ ID NOS: 7

<210> SEQ ID NO 1
<211> LENGTH: 3213
<212> TYPE: DNA
<213> ORGANISM: Homo sapiens

<400> SEQUENCE: 1
atgtgcttca gtttcataat gcctcctgct atggcagaca tccttgacat ctgggcggtg      60
gattcacaga tagcatctga tggctccata cctgtggatt tccttttgcc cactgggatt     120
tatatccagt tggaggtacc tcgggaagct accatttctt atattaagca gatgttatgg     180
aagcaagttc acaattaccc aatgttcaac ctccttatgg atattgactc ctatatgttt     240
gcatgtgtga atcagactgc tgtatatgag gagcttgaag atgaaacacg aagactctgt     300
gatgtcagac ctttctttcc agttctcaaa ttagtgacaa gaagttgtga cccagggaa      360 aaattagact caaaaattgg agtccttata ggaaaaggtc tgcatgaatt tgattccttg     420
aaggatcctg aagtaaatga atttcgaaga aaaatgcgca aattcagcga ggaaaaaatc     480
ctgtcacttg tgggattgtc ttggatggac tggctaaaac aaacatatcc accagagcat     540
gaaccatcca tccctgaaaa cttagaagat aaactttatg ggggaaagct catcgtagct     600
gttcattttg aaaactgcca ggacgtgttt agctttcaag tgtctcctaa tatgaatcct     660
atcaaagtaa atgaattggc aatccaaaaa cgtttgacta ttcatgggaa ggaagatgaa     720
gttagcccct atgattatgt gttgcaagtc agcgggagag tagaatatgt tttggtgat      780 catccactaa ttcagttcca gtatatccgg aactgtgtga tgaacagagc cctgccccat     840
tttatacttg tggaatgctg caagatcaag aaaatgtatg aacaagaaat gattgccata     900
gaggctgcca taaatcgaaa ttcatctaat cttcctcttc cattaccacc aaagaaaaca     960
cgaattattt ctcatgtttg ggaaaataac aaccctttcc aaattgtctt ggttaaggga    1020
aataaactta acacagagga aactgtaaaa gttcatgtca gggctggtct ttttcatggt    1080
actgagctcc tgtgtaaaac catcgtaagc tcagaggtat cagggaaaaa tgatcatatt    1140
tggaatgaac cactggaatt tgatattaat atttgtgact taccaagaat ggctcgatta    1200
tgttttgctg tttatgcagt tttggataaa gtaaaaacga agaaatcaac gaaaactatt    1260
aatccctcta aatatcagac catcaggaaa gctggaaaag tgcattatcc tgtagcgtgg    1320
gtaaatacga tggttttttga ctttaaagga caattgagaa ctggagacat aatattacac    1380
agctggtctt catttcctga tgaactcgaa gaaatgttga atccaatggg aactgttcaa    1440
acaaatccat atactgaaaa tgcaacagct ttgcatgtta aatttccaga gaataaaaaa    1500
caaccttatt attaccctcc cttcgataag attattgaaa aggcagctga gattgcaagc    1560
agtgatagtg ctaatgtgtc aagtcgaggt ggaaaaaagt ttcttcctgt attgaaagaa    1620
atcttggaca gggatcccct tgtctcaact gtgtgaaaatg aaatggatct tatttggact    1680
```

```
ttgcgacaag actgccgaga gattttccca caatcactgc caaaattact gctgtcaatc   1740
aagtggaata aacttgagga tgttgctcag cttcaggcgc tgcttcagat ttggcctaaa   1800
ctgccccccc gggaggccct agagcttctg gatttcaact atccagacca gtacgttcga   1860
gaatatgctg taggctgcct gcgacagatg agtgatgaag aactttctca atatctttta   1920
caactggtgc aagtgttaaa atatgagcct tttcttgatt gtgccctctc tagattccta   1980
ttagaaagag cacttggtaa tcggaggata gggcagtttc tattttggca tcttaggtca   2040
gaagtgcaca ttcctgctgt ctcagtacaa tttggtgtca tccttgaagc atactgccgg   2100
ggaagtgtgg ggcacatgaa agtgctttct aagcaggttg aagcactcaa taagttaaaa   2160
actttaaata gttaatcaa actgaatgcc gtgaagttaa acagagccaa agggaaggag   2220
gccatgcata cctgtttaaa acagagtgct taccgggaag ccctctctga cctgcagtca   2280
cccctgaacc catgtgttat cctctcagaa ctctatgttg aaaagtgcaa atacatggat   2340
tccaaaatga agcctttgtg gctggtatac aataacaagg tatttggtga ggattcagtt   2400
ggagtgattt ttaaaaatgg tgatgattta cgacaggata tgttgacact ccaaatgttg   2460
cgcttgatgg atttactctg gaaagaagct ggttttggatc ttcggatgtt gccttatggc   2520
tgtttagcaa caggagatcg ctctggcctc attgaagttg tgagcacctc tgaaacaatt   2580
gctgacattc agctgaacag tagcaatgtg gctgctgcag cagccttcaa caaagatgcc   2640
cttctgaact ggcttaaaga atacaactct ggggatgacc tggaccgagc cattgaggaa   2700
tttacactgt cctgtgctgg ctactgtgta gcttcttatg tccttgggat tggtgacaga   2760
catagtgaca acatcatggt caaaaaaact ggccagctct tccacattga ctttggacat   2820
attcttggaa atttcaaatc taagtttggc attaaaaggg agcgagtgcc ttttattctt   2880
acctatgatt tcatccatgt cattcaacaa ggaaaaacag gaaatacaga aaagtttggc   2940
cggttccgcc agtgttgtga ggatgcatat ctgattttac gacggcatgg gaatctcttc   3000
atcactctct ttgcgctgat gttgactgca gggcttcctg aactcacatc agtcaaagat   3060
atacagtatc ttaaggactc tcttgcatta gggaagagtg aagaagaagc actcaaacag   3120
tttaagcaaa aatttgatga ggcgctcagg gaaagctgga ctactaaagt gaactggatg   3180
gcccacacag ttcggaaaga ctacagatct taa                                3213
```

<210> SEQ ID NO 2
<211> LENGTH: 3213
<212> TYPE: DNA
<213> ORGANISM: Homo sapiens

<400> SEQUENCE: 2

```
atgtgcttca gtttcataat gcctcctgct atggcagaca tccttgacat ctgggcggtg     60
gattcacaga tagcatctga tggctccata cctgtggatt tccttttgcc cactgggatt    120
tatatccagt tggaggtacc tcgggaagct accatttctt atattaagca gatgttatgg    180
aagcaagttc acaattaccc aatgttcaac ctccttatgg atattgactc ctatatgttt    240
gcatgtgtga atcagactgc tgtatatgag gagcttgaag atgaaacacg aagactctgt    300
gatgtcagac ttttcttcc agttctcaaa ttagtgacaa gaagttgtga cccaggggaa    360
aaattagact caaaaattgg agtccttata ggaaaaggtc tgcatgaatt tgattccttg    420
aaggatcctg aagtaaatga atttcgaaga aaaatgcgca aattcagcga ggaaaaaatc    480
ctgtcacttg tgggattgtc ttggatggac tggctaaaac aaacatatcc accagagcat    540
gaaccatcca tccctgaaaa cttagaagat aaactttatg ggggaaagct catcgtagct    600
```

```
gttcattttg aaaactgcca ggacgtgttt agctttcaag tgtctcctaa tatgaatcct      660
atcaaagtaa atgaattggc aatccaaaaa cgtttgacta ttcatgggaa ggaagatgaa      720
gttagcccct atgattatgt gttgcaagtc agcgggagag tagaatatgt ttttggtgat      780
catccactaa ttcagttcca gtatatccgg aactgtgtga tgaacagagc cctgccccat      840
tttatacttg tggaatgctg caagatcaag aaaatgtatg aacaagaaat gattgccata      900
gaggctgcca taaatcgaaa ttcatctaat cttcctcttc cattaccacc aaagaaaaca      960
cgaattattt ctcatgtttg ggaaaataac aacccttttcc aaattgtctt ggttaaggga     1020
aataaactta acacagagga aactgtaaaa gttcatgtca gggctggtct ttttcatggt     1080
actgagctcc tgtgtaaaac catcgtaagc tcagaggtat cagggaaaaa tgatcatatt     1140
tggaatgaac cactggaatt tgatattaat atttgtgact taccaagaat ggctcgatta     1200
tgttttgctg tttatgcagt tttggataaa gtaaaaacga agaaatcaac gaaaactatt     1260
aatccctcta aatatcagac catcaggaaa gctggaaaag tgcattatcc tgtagcgtgg     1320
gtaaatacga tggttttttga ctttaaagga caattgagaa ctggagacat aatattacac     1380
agctggtctt catttcctga tgaactcgaa gaaatgttga atccaatggg aactgttcaa     1440
acaaatccat atactgaaaa tgcaacagct ttgcatgtta aatttccaga gaataaaaaa     1500
caaccttatt attaccctcc cttcgataag attattgaaa aggcagctga gattgcaagc     1560
agtgatagtg ctaatgtgtc aagtcgaggt ggaaaaaagt tcttcctgt attgaaagaa     1620 atcttggaca gggatccctt gtctcaactg tgtgaaaatg aaatggatct tatttggact     1680
ttgcgacaag actgccgaga gattttccca caatcactgc caaaattact gctgtcaatc     1740
aagtggaata aacttgagga tgttgctcag cttcaggcgc tgcttcagat ttggcctaaa     1800
ctgccccccc gggaggccct agagcttctg gatttcaact atccagacca gtacgttcga     1860
gaatatgctg taggctgcct gcgacagatg agtgatgaag aactttctca atatctttta     1920
caactggtgc aagtgttaaa atatgagcct tttcttgatt gtgccctctc tagattccta     1980
ttagaaagag cacttggtaa tcggaggata gggcagtttc tattttggca tcttaggtca     2040
gaagtgcaca ttcctgctgt ctcagtacaa tttggtgtca tccttgaagc atactgccgg     2100
ggaagtgtgg ggcacatgaa agtgctttct aagcaggttg aagcactcaa taagttaaaa     2160
actttaaata gtttaatcaa actgaatgcc gtgaagttaa acagagccaa agggaaggag     2220
gccatgcata cctgtttaaa acagagtgct taccgggaag ccctctctga cctgcagtca     2280
cccctgaacc catgtgttat cctctcagaa ctctatgttg aaaagtgcaa atacatggat     2340
tccaaaatga agcctttgtg gctggtatac aataacaagg tatttggtga ggattcagtt     2400
ggagtgattt ttagaaatgg tgatgattta cgacaggata tgttgacact ccaaatgttg     2460
cgcttgatgg atttactctg gaaagaagct ggtttggatc ttcggatgtt gccttatggc     2520
tgtttagcaa caggagatcg ctctggcctc attgaagttg tgagcacctc tgaaacaatt     2580
gctgacattc agctgaacag tagcaatgtg gctgctgcag cagccttcaa caaagatgcc     2640
cttctgaact ggcttaaaga atacaactct ggggatgacc tggaccgagc cattgaggaa     2700
tttacactgt cctgtgctgg ctactgtgta gcttcttatg tccttgggat tggtgacaga     2760
catagtgaca acatcatggt caaaaaaact ggccagctct tccacattga ctttggacat     2820
attcttggaa atttcaaatc taagtttggc attaaaaggg agcgagtgcc ttttattctt     2880
acctatgatt tcatccatgt cattcaacaa ggaaaaacag aaatacaga aaagtttggc     2940 cggttccgcc agtgttgtga ggatgcatat ctgatttac gacggcatgg gaatctcttc     3000
```

```
atcactctct tgcgctgat gttgactgca gggcttcctg aactcacatc agtcaaagat    3060
atacagtatc ttaaggactc tcttgcatta gggaagagtg aagaagaagc actcaaacag    3120
tttaagcaaa aatttgatga ggcgctcagg gaaagctgga ctactaaagt gaactggatg    3180
gcccacacag ttcggaaaga ctacagatct taa                                 3213
```

<210> SEQ ID NO 3
<211> LENGTH: 1070
<212> TYPE: PRT
<213> ORGANISM: Homo sapiens

<400> SEQUENCE: 3

```
Met Cys Phe Ser Phe Ile Met Pro Ala Met Ala Asp Ile Leu Asp
1               5                   10                  15

Ile Trp Ala Val Asp Ser Gln Ile Ala Ser Asp Gly Ser Ile Pro Val
                20                  25                  30

Asp Phe Leu Leu Pro Thr Gly Ile Tyr Ile Gln Leu Glu Val Pro Arg
            35                  40                  45

Glu Ala Thr Ile Ser Tyr Ile Lys Gln Met Leu Trp Lys Gln Val His
 50                  55                  60

Asn Tyr Pro Met Phe Asn Leu Leu Met Asp Ile Asp Ser Tyr Met Phe
 65                  70                  75                  80

Ala Cys Val Asn Gln Thr Ala Val Tyr Glu Glu Leu Glu Asp Glu Thr
                 85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Lys Lys Thr
305                 310                 315                 320

Arg Ile Ile Ser His Val Trp Glu Asn Asn Pro Phe Gln Ile Val
                325                 330                 335
```

-continued

Leu Val Lys Gly Asn Lys Leu Asn Thr Glu Thr Val Lys Val His
            340                 345                 350

Val Arg Ala Gly Leu Phe His Gly Thr Glu Leu Leu Cys Lys Thr Ile
            355                 360                 365

Val Ser Ser Glu Val Ser Gly Lys Asn Asp His Ile Trp Asn Glu Pro
            370                 375             380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                    405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
            435                 440                 445

Lys Gly Gln Leu Arg Thr Gly Asp Ile Ile Leu His Ser Trp Ser Ser
            450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
                    485                 490                 495

Glu Asn Lys Lys Gln Pro Tyr Tyr Pro Pro Phe Asp Lys Ile Ile
            500                 505                 510

Glu Lys Ala Ala Glu Ile Ala Ser Ser Asp Ser Ala Asn Val Ser Ser
            515                 520                 525

Arg Gly Gly Lys Lys Phe Leu Pro Val Leu Lys Glu Ile Leu Asp Arg
            530                 535                 540

Asp Pro Leu Ser Gln Leu Cys Glu Asn Glu Met Asp Leu Ile Trp Thr
545                 550                 555                 560

Leu Arg Gln Asp Cys Arg Glu Ile Phe Pro Gln Ser Leu Pro Lys Leu
                    565                 570                 575

Leu Leu Ser Ile Lys Trp Asn Lys Leu Glu Asp Val Ala Gln Leu Gln
            580                 585                 590

Ala Leu Leu Gln Ile Trp Pro Lys Leu Pro Arg Glu Ala Leu Glu
            595                 600                 605

Leu Leu Asp Phe Asn Tyr Pro Asp Gln Tyr Val Arg Glu Tyr Ala Val
            610                 615                 620

Gly Cys Leu Arg Gln Met Ser Asp Glu Glu Leu Ser Gln Tyr Leu Leu
625                 630                 635                 640

Gln Leu Val Gln Val Leu Lys Tyr Glu Pro Phe Leu Asp Cys Ala Leu
                    645                 650                 655

Ser Arg Phe Leu Leu Glu Arg Ala Leu Gly Asn Arg Arg Ile Gly Gln
            660                 665                 670

Phe Leu Phe Trp His Leu Arg Ser Glu Val His Ile Pro Ala Val Ser
            675                 680                 685

Val Gln Phe Gly Val Ile Leu Glu Ala Tyr Cys Arg Gly Ser Val Gly
            690                 695                 700

His Met Lys Val Leu Ser Lys Gln Val Glu Ala Leu Asn Lys Leu Lys
705                 710                 715                 720

Thr Leu Asn Ser Leu Ile Lys Leu Asn Ala Val Lys Leu Asn Arg Ala
                    725                 730                 735

Lys Gly Lys Glu Ala Met His Thr Cys Leu Lys Gln Ser Ala Tyr Arg
            740                 745                 750

Glu Ala Leu Ser Asp Leu Gln Ser Pro Leu Asn Pro Cys Val Ile Leu
            755                 760                 765

```
Ser Glu Leu Tyr Val Glu Lys Cys Lys Tyr Met Asp Ser Lys Met Lys
    770                 775                 780

Pro Leu Trp Leu Val Tyr Asn Asn Lys Val Phe Gly Glu Asp Ser Val
785                 790                 795                 800

Gly Val Ile Phe Lys Asn Gly Asp Asp Leu Arg Gln Asp Met Leu Thr
                805                 810                 815

Leu Gln Met Leu Arg Leu Met Asp Leu Leu Trp Lys Glu Ala Gly Leu
            820                 825                 830

Asp Leu Arg Met Leu Pro Tyr Gly Cys Leu Ala Thr Gly Asp Arg Ser
        835                 840                 845

Gly Leu Ile Glu Val Val Ser Thr Ser Glu Thr Ile Ala Asp Ile Gln
    850                 855                 860

Leu Asn Ser Ser Asn Val Ala Ala Ala Ala Phe Asn Lys Asp Ala
865                 870                 875                 880

Leu Leu Asn Trp Leu Lys Glu Tyr Asn Ser Gly Asp Asp Leu Asp Arg
                885                 890                 895

Ala Ile Glu Glu Phe Thr Leu Ser Cys Ala Gly Tyr Cys Val Ala Ser
                900                 905                 910

Tyr Val Leu Gly Ile Gly Asp Arg His Ser Asp Asn Ile Met Val Lys
                915                 920                 925

Lys Thr Gly Gln Leu Phe His Ile Asp Phe Gly His Ile Leu Gly Asn
    930                 935                 940

Phe Lys Ser Lys Phe Gly Ile Lys Arg Glu Arg Val Pro Phe Ile Leu
945                 950                 955                 960

Thr Tyr Asp Phe Ile His Val Ile Gln Gln Gly Lys Thr Gly Asn Thr
                965                 970                 975

Glu Lys Phe Gly Arg Phe Arg Gln Cys Cys Glu Asp Ala Tyr Leu Ile
                980                 985                 990

Leu Arg Arg His Gly Asn Leu Phe Ile Thr Leu Phe Ala Leu Met Leu
                995                 1000                1005

Thr Ala Gly Leu Pro Glu Leu Thr Ser Val Lys Asp Ile Gln Tyr
    1010                1015                1020

Leu Lys Asp Ser Leu Ala Leu Gly Lys Ser Glu Glu Glu Ala Leu
    1025                1030                1035

Lys Gln Phe Lys Gln Lys Phe Asp Glu Ala Leu Arg Glu Ser Trp
    1040                1045                1050

Thr Thr Lys Val Asn Trp Met Ala His Thr Val Arg Lys Asp Tyr
    1055                1060                1065

Arg Ser
    1070

<210> SEQ ID NO 4
<211> LENGTH: 1070
<212> TYPE: PRT
<213> ORGANISM: Homo sapiens

<400> SEQUENCE: 4

Met Cys Phe Ser Phe Ile Met Pro Pro Ala Met Ala Asp Ile Leu Asp
1               5                   10                  15

Ile Trp Ala Val Asp Ser Gln Ile Ala Ser Asp Gly Ser Ile Pro Val
            20                  25                  30

Asp Phe Leu Leu Pro Thr Gly Ile Tyr Ile Gln Leu Glu Val Pro Arg
        35                  40                  45

Glu Ala Thr Ile Ser Tyr Ile Lys Gln Met Leu Trp Lys Gln Val His
    50                  55                  60
```

```
Asn Tyr Pro Met Phe Asn Leu Leu Met Asp Ile Asp Ser Tyr Met Phe
 65                  70                  75                  80

Ala Cys Val Asn Gln Thr Ala Val Tyr Glu Glu Leu Glu Asp Glu Thr
                 85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
    130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Pro Lys Lys Thr
305                 310                 315                 320

Arg Ile Ile Ser His Val Trp Glu Asn Asn Asn Pro Phe Gln Ile Val
                325                 330                 335

Leu Val Lys Gly Asn Lys Leu Asn Thr Glu Glu Thr Val Lys Val His
            340                 345                 350

Val Arg Ala Gly Leu Phe His Gly Thr Glu Leu Leu Cys Lys Thr Ile
        355                 360                 365

Val Ser Ser Glu Val Ser Gly Lys Asn Asp His Ile Trp Asn Glu Pro
    370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
        435                 440                 445

Lys Gly Gln Leu Arg Thr Gly Asp Ile Ile Leu His Ser Trp Ser Ser
    450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
```

```
                    485                 490                 495
Glu Asn Lys Lys Gln Pro Tyr Tyr Pro Phe Asp Lys Ile Ile
                500                 505                 510
Glu Lys Ala Ala Glu Ile Ala Ser Ser Asp Ser Ala Asn Val Ser Ser
                515                 520                 525
Arg Gly Gly Lys Lys Phe Leu Pro Val Leu Lys Glu Ile Leu Asp Arg
                530                 535                 540
Asp Pro Leu Ser Gln Leu Cys Glu Asn Glu Met Asp Leu Ile Trp Thr
545                 550                 555                 560
Leu Arg Gln Asp Cys Arg Glu Ile Phe Pro Gln Ser Leu Pro Lys Leu
                565                 570                 575
Leu Leu Ser Ile Lys Trp Asn Lys Leu Glu Asp Val Ala Gln Leu Gln
                580                 585                 590
Ala Leu Leu Gln Ile Trp Pro Lys Leu Pro Arg Glu Ala Leu Glu
                595                 600                 605
Leu Leu Asp Phe Asn Tyr Pro Asp Gln Tyr Val Arg Glu Tyr Ala Val
                610                 615                 620
Gly Cys Leu Arg Gln Met Ser Asp Glu Leu Ser Gln Tyr Leu Leu
625                 630                 635                 640
Gln Leu Val Gln Val Leu Lys Tyr Glu Pro Phe Leu Asp Cys Ala Leu
                645                 650                 655
Ser Arg Phe Leu Leu Glu Arg Ala Leu Gly Asn Arg Arg Ile Gly Gln
                660                 665                 670
Phe Leu Phe Trp His Leu Arg Ser Glu Val His Ile Pro Ala Val Ser
                675                 680                 685
Val Gln Phe Gly Val Ile Leu Glu Ala Tyr Cys Arg Gly Ser Val Gly
                690                 695                 700
His Met Lys Val Leu Ser Lys Gln Val Glu Ala Leu Asn Lys Leu Lys
705                 710                 715                 720
Thr Leu Asn Ser Leu Ile Lys Leu Asn Ala Val Lys Leu Asn Arg Ala
                725                 730                 735
Lys Gly Lys Glu Ala Met His Thr Cys Leu Lys Gln Ser Ala Tyr Arg
                740                 745                 750
Glu Ala Leu Ser Asp Leu Gln Ser Pro Leu Asn Pro Cys Val Ile Leu
                755                 760                 765
Ser Glu Leu Tyr Val Glu Lys Cys Lys Tyr Met Asp Ser Lys Met Lys
                770                 775                 780
Pro Leu Trp Leu Val Tyr Asn Asn Lys Val Phe Gly Glu Asp Ser Val
785                 790                 795                 800
Gly Val Ile Phe Arg Asn Gly Asp Asp Leu Arg Gln Asp Met Leu Thr
                805                 810                 815
Leu Gln Met Leu Arg Leu Met Asp Leu Leu Trp Lys Glu Ala Gly Leu
                820                 825                 830
Asp Leu Arg Met Leu Pro Tyr Gly Cys Leu Ala Thr Gly Asp Arg Ser
                835                 840                 845
Gly Leu Ile Glu Val Val Ser Thr Ser Glu Thr Ile Ala Asp Ile Gln
                850                 855                 860
Leu Asn Ser Ser Asn Val Ala Ala Ala Ala Phe Asn Lys Asp Ala
865                 870                 875                 880
Leu Leu Asn Trp Leu Lys Glu Tyr Asn Ser Gly Asp Asp Leu Asp Arg
                885                 890                 895
Ala Ile Glu Glu Phe Thr Leu Ser Cys Ala Gly Tyr Cys Val Ala Ser
                900                 905                 910
```

```
Tyr Val Leu Gly Ile Gly Asp Arg His Ser Asp Asn Ile Met Val Lys
    915                 920                 925

Lys Thr Gly Gln Leu Phe His Ile Asp Phe Gly His Ile Leu Gly Asn
    930                 935                 940

Phe Lys Ser Lys Phe Gly Ile Lys Arg Glu Arg Val Pro Phe Ile Leu
945                 950                 955                 960

Thr Tyr Asp Phe Ile His Val Ile Gln Gln Gly Lys Thr Gly Asn Thr
                965                 970                 975

Glu Lys Phe Gly Arg Phe Arg Gln Cys Cys Glu Asp Ala Tyr Leu Ile
                980                 985                 990

Leu Arg Arg His Gly Asn Leu Phe  Ile Thr Leu Phe Ala Leu Met Leu
            995                 1000                1005

Thr Ala  Gly Leu Pro Glu Leu  Thr Ser Val Lys Asp  Ile Gln Tyr
    1010                1015                1020

Leu Lys  Asp Ser Leu Ala Leu  Gly Lys Ser Glu Glu  Glu Ala Leu
    1025                1030                1035

Lys Gln  Phe Lys Gln Lys Phe  Asp Glu Ala Leu Arg  Glu Ser Trp
    1040                1045                1050

Thr Thr  Lys Val Asn Trp Met  Ala His Thr Val Arg  Lys Asp Tyr
    1055                1060                1065

Arg Ser
    1070

<210> SEQ ID NO 5
<211> LENGTH: 816
<212> TYPE: DNA
<213> ORGANISM: Artificial Sequence
<220> FEATURE:
<223> OTHER INFORMATION: synthetic probe 1 to detect homologous
      recombination
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 5
ctggtccggg cccccctcg aggtcgacgg tatcgataag cttgatatcg aattcctgca      60
ggtaagaaag taagtngtca ggtaatacat gcttctaatt aatggtgagg ctgtaagagg    120
tgggaaggtt tctgcaagtt cctgtgttca gtgtaagact cctgcctggc ccagcctcca    180
aaagaaaaaa atgttgtcca gtagttttca tgagcaaaaa tgaaaaccta cagactatct    240
attaagtctt gtaacttgta aaacacatgt tcttctcatg ccatacgact gggactgaaa    300
cactgactct ctggggtctt cagccagact tcagacacga tccgtgttca tgagtcgtga    360
acattgcaag ttctcagcct ttctgactca gacaaagaac taaccactgg ctcccttgtg    420
tctccagctt gtcaactttg cagatcctga cgtgccattg tatacttcca aaaccattca    480
agacagatct tgctagtaag tcgccaaata catctgtgtg ttctgatgta tctatgatac    540
atgtcaatag tcacatgtaa gcatgcacag tgatcctctc ttagccgttc gttgttacag    600
gaaaccctcg ggcattcacg cacctgtctc ttctgttgt aatgcacatc tcagccaagg    660
gagtcagaaa agaaaaggct gggagagatg cgcgaangtg ttgttttttt gtttttact    720 tttattaac acagaactag agcacccaac ctttctagca atctgcatct gcagcccggg    780
ggatccacca gtctagacgc cgccaccgcg ggagac                              816
```

```
<210> SEQ ID NO 6
<211> LENGTH: 412
<212> TYPE: DNA
<213> ORGANISM: Artificial Sequence
<220> FEATURE:
<223> OTHER INFORMATION: synthetic probe 2 to detect Cre-mediated
      excision

<400> SEQUENCE: 6
agcagccttc aacaaagatg cccttctgaa ctggcttaaa gaatacaact ctggggatga      60
cctggaccga gccattgagg aatttacact gtcctgtgct ggctactgtg tagcttctta     120
tgtccttggg attggtgaca gacatagtga caacatcatg gtcaaaaaaa ctggccagct     180
cttccacatt gactttggac atattcttgg aaatttcaaa tctaagtttg gcattaaaag     240
ggagcgagtg cctttattc ttacctatga tttcatccat gtcattcaac aaggaaaaac      300
aggaaataca gaaaagtttg gccggttccg ccagtgttgt gaggatgcat atctgatttt     360
acgacggcat gggaatctct tcatcactct ctttgcgctg atgttgactg ca             412

<210> SEQ ID NO 7
<211> LENGTH: 11
<212> TYPE: PRT
<213> ORGANISM: Artificial Sequence
<220> FEATURE:
<223> OTHER INFORMATION: consensus in ATP-binding site of PI3KB from
      different species

<400> SEQUENCE: 7

Phe Lys Asn Gly Asp Asp Leu Arg Gln Asp Met
1               5                   10
```